United States Patent
Guo et al.

(10) Patent No.: US 11,371,077 B2
(45) Date of Patent: Jun. 28, 2022

(54) HIGH THROUGHPUT CELL-BASED SCREENING FOR APTAMERS

(71) Applicant: MeiraGTx UK II Limited, London (GB)

(72) Inventors: Xuecui Guo, Cold Spring Harbor, NY (US); Alexandria Forbes, New York, NY (US); Lei Feng, Bronx, NY (US)

(73) Assignee: MEIRAGTX UK II LIMITED, London (GB)

( * ) Notice: Subject to any disclaimer, the term of this patent is extended or adjusted under 35 U.S.C. 154(b) by 0 days.

(21) Appl. No.: 16/322,865

(22) PCT Filed: Aug. 3, 2017

(86) PCT No.: PCT/IB2017/001113
§ 371 (c)(1),
(2) Date: Feb. 1, 2019

(87) PCT Pub. No.: WO2018/025085
PCT Pub. Date: Feb. 8, 2018

(65) Prior Publication Data
US 2020/0239940 A1  Jul. 30, 2020

Related U.S. Application Data

(60) Provisional application No. 62/370,599, filed on Aug. 3, 2016.

(51) Int. Cl.
*C12Q 1/6811* (2018.01)
*C12N 15/115* (2010.01)
*C12N 15/10* (2006.01)

(52) U.S. Cl.
CPC ........ *C12Q 1/6811* (2013.01); *C12N 15/1048* (2013.01); *C12N 15/115* (2013.01); *C12N 2310/16* (2013.01); *C12N 2320/11* (2013.01); *C12N 2330/31* (2013.01)

(58) Field of Classification Search
None
See application file for complete search history.

(56) References Cited

U.S. PATENT DOCUMENTS

| | | | |
|---|---|---|---|
| 10,494,646 B2* | 12/2019 | Boyne | C12Y 105/01003 |
| 2003/0027184 A1* | 2/2003 | Gorenstein | C12N 15/115 435/6.11 |
| 2004/0126882 A1 | 7/2004 | Ellington et al. | |
| 2005/0197311 A1 | 9/2005 | Cooper et al. | |
| 2008/0269258 A1* | 10/2008 | Breaker | A61P 31/04 514/263.3 |
| 2009/0264508 A1* | 10/2009 | Sullenger | A61P 35/00 514/44 R |
| 2010/0184810 A1 | 7/2010 | Breaker et al. | |
| 2010/0221821 A1 | 9/2010 | Breaker et al. | |
| 2011/0111411 A1 | 5/2011 | Smolke et al. | |
| 2015/0175981 A1 | 6/2015 | Olsen | |
| 2018/0155775 A1* | 6/2018 | Zimmermann | C12Q 1/6806 |

FOREIGN PATENT DOCUMENTS

| | | | |
|---|---|---|---|
| JP | 2006-500933 A | 1/2006 | |
| JP | 2008-518630 A | 6/2008 | |
| WO | 2004028464 A2 | 4/2004 | |
| WO | 2006055351 A2 | 5/2006 | |
| WO | WO-2014110006 A1 * | 7/2014 | ......... C12N 15/1093 |
| WO | 2016/126747 A1 | 8/2016 | |
| WO | 2016/166303 A1 | 10/2016 | |

OTHER PUBLICATIONS

Groher et al. Biochimica et Biphysica Acta 1839, 964-973 (Year: 2014).*
Hall et al. Current Protocols in Molecular Biology 24.2.1.-24.2.27, Supplement 88, pp. 1-27 (Year: 2009).*
Andrew Wachter RNA Biology 7:1, 67-76 (Year: 2010).*
Bocobza, S., et al., "Riboswitch-Dependent Gene Regulation and its Evolution in the Plant Kingdom"; Genes & Dev. (2007); vol. 21; pp. 2874-2879.
Cheah, M. T., et al., "Control of Alternative RNA Splicing and Gene Expression by Eukaryotic Riboswitches", Nature (2007); vol. 447; pp. 497-501.
Cheah, M. T., et al., "Supplementary Information: Control of Alternative RNA Splicing and Gene Expression by Eukaryotic Riboswitches"; Nature (2007); vol. 447:7143; 18 pgs.
Culler, S. J. et al., "Reprogramming Cellular Behavior with RNA Controllers Responsive to Endogenous Proteins"; Science (2010); vol. 330; pp. 1251-1255.
Croft, M. T., Thiamine Biosynthesis in Algae is Regulated by Riboswitches; PNAS (2007); vol. 104:52; pp. 20770-20775.
Kotula, J. W. "Aptamer-Mediated Delivery of Splice-Switching Oligonucleotides to the Nuclei of Cancer Cells"; Nucleic Acid Thep. (2012); vol. 22:3; pp. 187-195.
Thompson, K. M. et al., "Group I Aptazymes as Generic Regulatory Switches"; BMC Biotech. (2002); vol. 2:21, 12 pgs.
Wang, Z. et al., "Systematic Identification and Analysis of Exonic Splicing Silencers"; Cell (2004); vol. 119; pp. 831-345.
Weigand, J. E., "Tetracycline Aptamer-Controlled Regulation of Pre-mRNA Splicing in Yeast"; NAR (2007); vol. 35:12; pp. 4179-4185.

(Continued)

*Primary Examiner* — Brian Whiteman
(74) *Attorney, Agent, or Firm* — Fox Rothschild LLP

(57) ABSTRACT

The invention provides eukaryotic cell-based screening methods to identify an aptamer that specifically binds a ligand, or a ligand that specifically binds an aptamer, using a polynucleotide cassette for the regulation of the expression of a reporter gene where the polynucleotide cassette contains a riboswitch in the context of a 5' intron-alternative exon-3' intron. The riboswitch comprises an effector region and an aptamer such that when the aptamer binds a ligand, reporter gene expression occurs.

39 Claims, 17 Drawing Sheets

Specification includes a Sequence Listing.

(56) References Cited

OTHER PUBLICATIONS

Kimoto, M. et al., "Generation of High-Affinity DNA Aptapers using an Expanded Genetic Alphabet"; Nature Biotechnology (2013); vol. 31:5; pp. 453-458.

* cited by examiner

* Denotes randomized region

Template for generating randomized aptamer sequence

Strategy of Splitting Randomized Aptamer Library by Sequencing Tagging and PCR Amplification

*Denotes Randomized Region

I.

II.

III.

Two-cycle PCR to add sequence tags

Tagged template

Generation of tagged aptamer library

HIGH THROUGHPUT CELL-BASED SCREENING FOR APTAMERS

FIELD OF THE INVENTION

The invention provides screening methods to identify an aptamer that specifically binds a ligand, or a ligand that specifically binds an aptamer, in a eukaryotic cell using a polynucleotide cassette for the regulation of the expression of a reporter gene where the polynucleotide cassette contains a riboswitch in the context of a 5' intron-alternative exon-3' intron. The riboswitch comprises an effector region and an aptamer such that when the aptamer binds a ligand, reporter gene expression occurs.

BACKGROUND OF THE INVENTION

Splicing refers to the process by which intronic sequence is removed from the nascent pre-messenger RNA (pre-mRNA) and the exons are joined together to form the mRNA. Splice sites are junctions between exons and introns, and are defined by different consensus sequences at the 5' and 3' ends of the intron (i.e., the splice donor and splice acceptor sites, respectively). Alternative pre-mRNA splicing, or alternative splicing, is a widespread process occurring in most human genes containing multiple exons. It is carried out by a large multi-component structure called the spliceosome, which is a collection of small nuclear ribonucleoproteins (snRNPs) and a diverse array of auxiliary proteins. By recognizing various cis regulatory sequences, the spliceosome defines exon/intron boundaries, removes intronic sequences, and splices together the exons into a final translatable message (i.e., the mRNA). In the case of alternative splicing, certain exons can be included or excluded to vary the final coding message thereby changing the resulting expressed protein.

The present invention utilizes ligand/aptamer-mediated control of alternative splicing to identify aptamer/ligand pairs that bind in the context of a target eukaryotic cell. Prior to the present invention, aptamers have been generated against a variety of ligands through in vitro screening, however, few have proved to be effective in cells, highlighting a need for systems to screen aptamers that function in the organism of choice.

SUMMARY OF THE INVENTION

In one aspect, the present invention provides a method for selecting an aptamer that binds a ligand in eukaryotic cells comprising the steps of:
  (a) providing a library of aptamers,
  (b) introducing members of the library of aptamers into a polynucleotide cassette for the ligand-mediated expression of a reporter gene to create a library of riboswitches,
  (c) introducing the library of riboswitches into eukaryotic cells, and
  (d) contacting the eukaryotic cells with a ligand, and
  (e) measuring expression of the reporter gene,
wherein the polynucleotide cassette comprises an alternatively-spliced exon, flanked by a 5' intron and a 3' intron, and a riboswitch comprising (i) an effector region comprising a stem that includes the 5' splice site of the 3' intron, and (ii) an aptamer, wherein the alternatively-spliced exon comprises a stop codon that is in-frame with the reporter gene when the alternatively-spliced exon is spliced into the reporter gene mRNA.

In one embodiment, the library of aptamers comprises aptamers having one or more randomized nucleotides. In one embodiment, the library of aptamers comprises aptamers having fully randomized sequences. In one embodiment, the library of aptamers comprises aptamers that are between about 15 to about 200 nucleotides in length. In one embodiment, the library of aptamers comprises aptamers that are between about 30 and about 100 nucleotides in length. In one embodiment, the library of aptamers comprises more than 100,000 aptamers. In one embodiment, the library of aptamers comprises more than 1,000,000 aptamers.

In one embodiment, the ligand is a small molecule. In one embodiment, the small molecule ligand is exogenous to the eukaryotic cell. In another embodiment, the ligand is a molecule produced by the eukaryotic cell including, e.g., a metabolite, nucleic acid, vitamin, co-factor, lipid, monosaccharide, and second messenger.

In one embodiment, the eukaryotic cell is selected from a mammalian cell, an insect cell, a plant cell, and a yeast cell. In one embodiment, the eukaryotic cell is derived from a mouse, a human, a fly (e.g., *Drosophila melanogaster*), a fish (e.g., *Danio rerio*) or a nematode worm (e.g., *Caenorhabditis elegans*).

In one embodiment, the reporter gene is selected from the group consisting of a fluorescent protein, luciferase, β-galactosidase and horseradish peroxidase. In one embodiment, the reporter gene is a cytokine, a signaling molecule, a growth hormone, an antibody, a regulatory RNA, a therapeutic protein, or a peptide. In one embodiment, the expression of the reporter gene is greater than about 10-fold higher when the ligand specifically binds the aptamer than the reporter gene expression levels when the ligand is absent. In further embodiments, the expression of the reporter gene is greater than about 20, 50, 100, 200, 500, or 1,000-fold higher when the ligand specifically binds the aptamer than the reporter gene expression levels when the ligand is absent.

In one embodiment, the 5' and 3' introns are derived from intron 2 of the human β-globin gene. In one embodiment, the 5' intron comprises a stop codon in-frame with the target gene. In one embodiment, the 5' and 3' introns are each independently from about 50 to about 300 nucleotides in length. In one embodiment, the 5' and 3' introns are each independently from about 125 to about 240 nucleotides in length. In one embodiment, the 5' and/or 3' introns have been modified to include, or alter the sequence of, an intron splice enhancer, an intron splice enhancer, a 5' splice site, a 3' splice site, or the branch point sequence.

In one embodiment, the effector region stem of the riboswitch is about 7 to about 20 base pairs in length. In one embodiment, the effector region stem is 8 to 11 base pairs in length.

In one embodiment, the alternatively-spliced exon is derived from exon 2 of the human dihydrofolate reductase gene (DHFR), mutant human Wilms tumor 1 exon 5, mouse calcium/calmodulin-dependent protein kinase II delta exon 16, or SIRT1 exon 6. In one embodiment, the alternatively-spliced exon is the modified DHFR exon 2. In one embodiment, the alternatively-spliced exon has been modified in one or more of the group consisting of altering the sequence of an exon splice silencer, altering the sequence of an exon splice enhancer, adding an exon splice enhancer, and adding an exon splice donor. In one embodiment, the alternatively-spliced exon is synthetic (i.e., not derived from a naturally-occurring exon).

In one embodiment, the library of aptamers is divided into a smaller aptamer library before introducing into the polynucleotide cassettes comprising the steps:
(a) providing a randomized aptamer library wherein the aptamers in the library comprise multiple 5' and 3' constant regions and one or more randomized nucleotides,
(b) performing a two-cycle PCR using the randomized aptamer library as the template and a first primer and second primer that are complementary to the 5' and 3' constant regions,
(c) isolating the products of the two-cycle PCR, and
(d) PCR amplifying a subset of the isolated products of the two-cycle PCR using multiple of primers complementary to a subset of the unique 5' and 3' constant regions.

In one embodiment, the library of riboswitches is divided into one or more sub-libraries of riboswitches before being introduced into the eukaryotic cells. In one embodiment, the method for dividing the riboswitch library into sub-libraries comprises the steps of:
(a) introducing a library of aptamers into a plasmid comprising a gene regulation polynucleotide cassette to make riboswitch library;
(b) introducing the riboswitch library into bacteria (e.g., *E. coli*); and
(c) collecting bacterial clones (for example by picking bacterial colonies) and extracting plasmid DNA to obtain plasmid sub-libraries of riboswitches (referred to herein as primary sub-libraries);

In embodiments, secondary sub-libraries of riboswitches are generated from a primary plasmid sub-library of riboswitches by introducing a primary sub-library into bacteria, collecting bacterial clones and isolating the plasmid DNA. The primary or secondary sub-library are then introduced into eukaryotic cells, the eukaryotic cells contacted with a ligand, and expression of the reporter gene measured to determine whether one or more aptamers in the library bind the ligand in the context of the eukaryotic cell.

In one embodiment, the present invention includes an aptamer that binds a target ligand wherein the aptamer is selected by the above methods. In embodiments of the invention, the aptamer comprises the sequence of SEQ ID NO: 14 to 27. In one embodiment, the aptamer sequence comprises the sequence of SEQ ID NO: 24.

In another aspect, the invention provides a method for selecting a ligand that binds an aptamer in a eukaryotic cell comprising the steps of:
(a) providing a library of ligands,
(b) providing a polynucleotide cassette for the ligand-mediated expression of a reporter gene,
(c) introducing the polynucleotide cassette into the eukaryotic cell,
(d) contacting individual groups of the eukaryotic cell with members of the library of ligands, and
(e) measuring the expression of the reporter gene,
wherein the polynucleotide cassette comprises an alternatively-spliced exon, flanked by a 5' intron and a 3' intron, and a riboswitch comprising (i) an effector region comprising a stem that includes the 5' splice site of the 3' intron, and (ii) an aptamer, wherein the alternatively-spliced exon comprises a stop codon that is in-frame with the reporter gene when the alternatively-spliced exon is spliced into the reporter gene mRNA.

In one embodiment, the ligand is a small molecule. In one embodiment, the small molecule ligand is exogenous to the eukaryotic cell. In another embodiment, the ligand is a molecule produced by the eukaryotic cell including, e.g., a metabolite, nucleic acid, vitamin, co-factor, lipid, monosaccharide, and second messenger.

In one embodiment, the eukaryotic cell is selected from a mammalian cell, an insect cell, a plant cell, and a yeast cell. In one embodiment the eukaryotic cell is derived from a mouse, a human, a fly (e.g., *Drosophila melanogaster*), a fish (e.g., *Danio rerio*) or a nematode worm (e.g., *Caenorhabditis elegans*).

In one embodiment, the reporter gene is selected from the group consisting of a fluorescent protein, luciferase, β-galactosidase and horseradish peroxidase. In one embodiment the reporter gene is a cytokine, a signaling molecule, a growth hormone, an antibody, a regulatory RNA, a therapeutic protein, or a peptide. In one embodiment, the expression of the reporter gene is greater than about 10-fold higher when the ligand specifically binds the aptamer than the reporter gene expression levels when the ligand is absent. In further embodiments, the expression of the reporter gene is greater than about 20, 50, 100, 200, 500, or 1,000-fold higher when the ligand specifically binds the aptamer than the reporter gene expression levels when the ligand is absent.

In one embodiment, the 5' and 3' introns are derived from intron 2 of the human β-globin gene. In one embodiment, the 5' intron comprises a stop codon in-frame with the target gene. In one embodiment, the 5' and 3' introns are each independently from about 50 to about 300 nucleotides in length. In one embodiment, the 5' and 3' introns are each independently from about 125 to about 240 nucleotides in length. In one embodiment, the 5' and/or 3' introns have been modified to include, or alter the sequence of, an intron splice enhancer, an exon splice enhancer, a 5' splice site, a 3' splice site, or the branch point sequence.

In one embodiment, the effector region stem of the riboswitch is about 7 to about 20 base pairs in length. In one embodiment, the effector region stem is 8 to 11 base pairs in length.

In one embodiment, the alternatively-spliced exon is derived from exon 2 of the human dihydrofolate reductase gene (DHFR), mutant human Wilms tumor 1 exon 5, mouse calcium/calmodulin-dependent protein kinase II delta exon 16, or SIRT1 exon 6. In one embodiment, the alternatively-spliced exon is a modified DHFR exon 2. In one embodiment, the alternatively-spliced exon has been modified in one or more of the group consisting of altering the sequence of an exon splice silencer, altering the sequence of an exon splice enhancer, adding an exon splice enhancer, and adding an exon splice donor. In one embodiment, the alternatively-spliced exon is synthetic (i.e., not derived from a naturally-occurring exon).

In one embodiment, the present invention includes a ligand selected by the above methods.

In another aspect the invention provides a method for splitting a randomized aptamer library into smaller aptamer sub-libraries comprising the steps:
(a) providing a randomized aptamer library wherein the aptamers in the library comprise multiple 5' and 3' constant regions and one or more randomized nucleotides,
(b) performing a two-cycle PCR using the randomized aptamer library as the template and first primers and second primers that are complementary to the 5' and 3' constant regions,
(c) isolating the products of the two-cycle PCR, and (d) PCR amplifying a subset of the isolated products of the two-cycle PCR using primers complementary to a subset of the unique 5' and 3' constant regions.

In one embodiment, the randomized aptamer library comprises aptamers having one or more randomized nucleotides. In one embodiment, the randomized aptamer library comprises more than about 100,000 aptamers. In one embodiment, the randomized aptamer library comprises more than about 1,000,000 aptamers.

In one embodiment, the first or second primer in the two-cycle PCR comprises a label selected from the group consisting of biotin, digoxigenin (DIG), bromodeoxyuridine (BrdU), fluorophore, a chemical group, e.g. thiol group, or a chemical group e.g. azides used in Click Chemistry

BRIEF DESCRIPTION OF THE FIGURES

FIG. 3a. The schematic diagram of the two-step strategy for splitting a large aptamer library. The first step is to add a unique pair of sequence tags to each aptamer oligonucleotide template. Following the first step, templates with unique tag sequences are amplified using primers that are specific to tagged sequences.

FIG. 3b. Three approaches to attaching tag sequences to templates: tag sequences incorporated through PCR using primers that contain tag sequences at the 5' end of primers (I); tag sequences attached by ligating single stranded template sequence with single stranded tag sequences by T4 RNA ligase (II); tag sequences linked to templates by ligating double stranded template sequences with double stranded tag sequence by T4 DNA ligase (III).

FIG. 3c. Schematic diagram of two-cycle PCR. For cycle 1, only reverse primers JR which contain tag sequence at 5' end. After the first cycle, the newly synthesized strand has a sequence tag at its 5' end. For cycle 2, biotin labeled forward primer JF is added to the PCR reaction, which can only use the newly synthesized strand as template, thus generating the templates with tag sequences at both 5' and 3' ends and a biotin molecule at 5' end.

FIG. 3d. Generation of tagged aptamer library. After labeling templates with sequence tags and biotin molecule, streptavidin beads are used to separate the labeled/tagged single stranded templates from the rest of the reaction components through denaturing the oligos and beads washing. Then the tagged templates are amplified and expanded using a mixture of primers (F and R primers) that are specific to the tagged sequences, thus generating tagged aptamer library that are ready for subsequent PCR using a single pair of tag sequence-specific primers to generate sub-libraries of the original aptamer library.

FIG. 3e. Sub-libraries of aptamers are PCR amplified using the splitting strategy. Aptamer library ($10^6$, generated as in Example 2) was tagged by PCR using 2 forward primers (JF1-2) and 8 reverse primers (JR1-8), with template copy number at 1, 2.3 or 4.6. The isolated tagged templates were expanded by a mixture of tag-specific primers F1-2 and R1-8, and the PCR products were subject to PCR with either universal primers (left panel), single pair of tag-specific primers F1 and R1 (middle panel), or single pair non-relevant primers of F3 and R1 (right panel). Water was used as blank control for templates.

DETAILED DESCRIPTION OF THE INVENTION

Methods of Screening Aptamer/Ligand

Figure 1A:
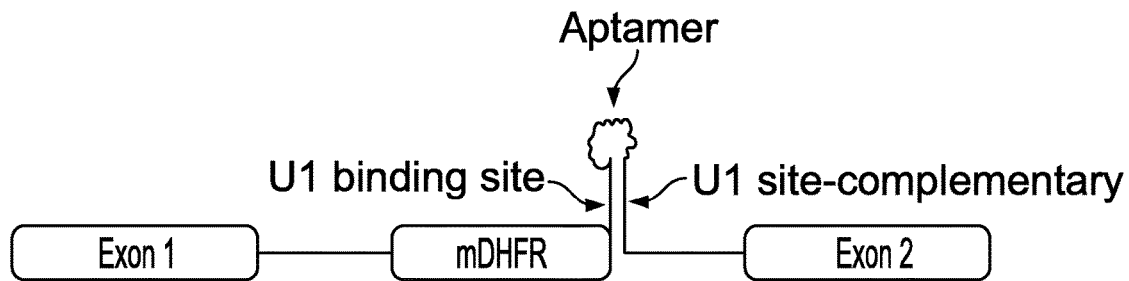
FIG. 1a. Schematic of the riboswitch construct. A truncated beta-globin intron sequence was inserted in the coding sequence of the reporter gene, and a mutant, stop-codon containing DHFR exon 2 (mDHFR) was placed in the inserted intron, thus forming a three-exon gene expression platform by which the reporter gene expression is regulated by inclusion/exclusion of the mDHFR exon. A hairpin/stem structure is formed including the U1 binding site in the intron downstream (3') of the mDHFR exon with the engineered sequence complementary to the U1 binding site, which blocks the U1 binding, thereby leading to the exclusion of stop-codon containing mDHFR exon and target gene expression. The aptamer sequence is grafted in between the U1 binding site and its complementary sequence, allowing the control of hairpin formation by aptamer/ligand binding.

The present invention provides screening methods to identify aptamers that bind to a ligand, and ligands that bind to an aptamer, in the context of a eukaryotic cell, tissue, or organism. In one aspect, the present invention provides a method for selecting an aptamer that binds a ligand in eukaryotic cells comprising the steps of:
  (a) providing a library of aptamers,
  (b) introducing members of the library of aptamers into polynucleotide cassettes for the ligand-mediated expression of a reporter gene,
  (c) introducing the aptamer containing polynucleotide cassettes into eukaryotic cells, and
  (d) contacting the eukaryotic cells with a ligand, and
  (e) measuring expression of the reporter gene.

In another aspect, the invention provides a method for selecting a ligand that binds an aptamer in a eukaryotic cell comprising the steps of:
  (a) providing a library of ligands,
  (b) providing a polynucleotide cassette for the ligand-mediated expression of a reporter gene,
  (c) introducing the polynucleotide cassette into the eukaryotic cell,
  (d) contacting individual groups of the eukaryotic cell with members of the library of ligands, and
  (e) measuring the expression of the reporter gene.

In one embodiment, the invention provides methods to identify aptamers that bind to intracellular molecules comprising the steps of:
  (a) providing a library of aptamers,
  (b) introducing members of the library of aptamers into polynucleotide cassettes for the ligand-mediated expression of a reporter gene,
  (c) introducing the aptamer containing polynucleotide cassettes into eukaryotic cells, and
  (d) measuring expression of the reporter gene.

The screening methods of the present invention utilize the gene regulation polynucleotide cassettes disclosed in PCT/US2016/016234, which is incorporated in its entirety herein by reference. These gene regulation cassettes comprise a riboswitch in the context of a 5' intron-alternative exon-3' intron. The gene regulation cassette refers to a recombinant DNA construct that, when incorporated into the DNA of a target gene (e.g., a reporter gene), provides the ability to regulate expression of the target gene by aptamer/ligand mediated alternative splicing of the resulting pre-mRNA. The gene regulation cassette further comprises a riboswitch containing a sensor region (e.g., an aptamer) and an effector region that together are responsible for sensing the presence of a ligand that binds the aptamer and altering splicing to an alternative exon. These aptamer-driven riboswitches provide regulation of mammalian gene expression at a 2- to 2000-fold induction, in responding to treatment with the ligand that binds the aptamer. The unprecedented high dynamic regulatory range of this synthetic riboswitch is used in methods of the present invention to provide screening systems for new aptamers against desired types of ligands, as well as for optimal ligands against known and novel aptamers in cells, tissues and organisms.

Riboswitch

The term "riboswitch" as used herein refers to a regulatory segment of a RNA polynucleotide (or the DNA encoding the RNA polynucleotide). A riboswitch in the context of the present invention contains a sensor region (e.g., an aptamer) and an effector region that together are responsible for sensing the presence of a ligand (e.g., a small molecule) and altering splicing to an alternative exon. In one embodiment, the riboswitch is recombinant, utilizing polynucleotides from two or more sources. The term "synthetic" as used herein in the context of a riboswitch refers to a riboswitch that is not naturally occurring. In one embodiment, the sensor and effector regions are joined by a polynucleotide linker. In one embodiment, the polynucleotide linker forms a RNA stem (i.e., a region of the RNA polynucleotide that is double-stranded).

A library of riboswitches as described herein comprise a plurality of aptmer sequences that differ by one or more nucleotides in the contect of the polynucleotide cassettes for the ligand-mediated expression of a reporter gene. Thus, each aptamer in the library, along with a sensor region, is in the context of a 5' intron-alternative exon-3' intron as described herein.

Effector Region

In one embodiment, the effector region comprises the 5' splice site ("5' ss") sequence of the 3' intron (i.e., the intronic splice site sequence that is immediately 3' of the alternative exon). The effector region comprises the 5' ss sequence of the 3' intron and sequence complimentary to the 5' ss sequence of the 3' intron. When the aptamer binds its ligand, the effector region forms a stem and thus prevents splicing to the splice donor site at the 3' end of the alternative exon. Under certain conditions (for example, when the aptamer is not bound to its ligand), the effector region is in a context that provides access to the splice donor site at the 3' end of the alternative exon leading to inclusion of the alternative exon in the target gene mRNA.

The stem portion of the effector region should be of a sufficient length (and GC content) to substantially prevent alternative splicing of the alternative exon upon ligand binding the aptamer, while also allowing access to the splice site when the ligand is not present in sufficient quantities. In embodiments of the invention, the stem portion of the effector region comprises stem sequence in addition to the 5' ss sequence of the 3' intron and its complementary sequence. In embodiments of the invention, this additional stem sequence comprises sequence from the aptamer stem. The length and sequence of the stem portion can be modified using known techniques in order to identify stems that allow acceptable background expression of the target gene when no ligand is present and acceptable expression levels of the target gene when the ligand is present. If the stem is, for example, too long it may hide access to the 5' ss sequence of the 3' intron in the presence or absence of ligand. If the stem is too short, it may not form a stable stem capable of sequestering the 5' ss sequence of the 3' intron, in which case the alternative exon will be spliced into the target gene message in the presence or absence of ligand. In one embodiment, the total length of the effector region stem is between about 7 base pairs to about 20 base pairs. In some embodiments, the length of the stem is between about 8 base pairs to about 11 base pairs. In some embodiments, the length of the stem is 8 base pairs to 11 base pairs. In addition to the length of the stem, the GC base pair content of the stem can be altered to modify the stability of the stem.

Aptamer/Ligand

The term "aptamer" as used herein refers to an RNA polynucleotide (or the DNA encoding the RNA polynucleotide) that specifically binds to a ligand or to an RNA polynucleotide that is being screened to identify specific binding to a ligand (i.e., a prospective aptamer). A library of aptamers is a collection of prospective aptamers comprising multiple prospective aptamers having a nucleotide sequence that differs from other members of the library by at least one nucleotide.

The term "ligand" refers to a molecule that is specifically bound by an aptamer, or to a prospective ligand that is being screened for the ability to bind to one or more aptamers. A library of ligands is a collection of ligands and/or prospective ligands.

In one embodiment, the ligand is a low molecular weight (less than about 1,000 Daltons) molecule including, for example, lipids, monosaccharides, second messengers, co-factors, metal ions, other natural products and metabolites, nucleic acids, as well as most therapeutic drugs. In one embodiment, the ligand is a polynucleotide with 2 or more nucleotide bases.

In one embodiment, the ligand is selected from the group consisting of 8-azaguanine, adenosine 5'-monophosphate monohydrate, amphotericin B, avermectin B1, azathioprine, chlormadinone acetate, mercaptopurine, moricizine hydrochloride, N6-methyladenosine, nadide, progesterone, promazine hydrochloride, pyrvinium pamoate, sulfaguanidine, testosterone propionate, thioguanosine, Tyloxapol and Vorinostat.

In certain embodiments, the methods of the present invention are used to identify a ligand that is an intracellular molecule that binds to the aptamer (i.e., an endogenous ligand) in the polynucleotide cassette thereby causing expression of the reporter gene. For example, cells with a reporter gene containing the polynucleotide cassette for the aptamer/ligand mediated expression, can be exposed to a condition, such as heat, growth, transformation, or mutation, leading to changes in cell signaling molecules, metabolites, peptides, lipids, ions (e.g., $Ca^{2+}$), etc. that can bind to the aptamer and cause expression of the reporter gene. Thus, the methods of the present invention, can be used to identify aptamers that bind to intracellular ligands in response to changes in cell state, including, e.g., a change in cell signaling, cell metabolism, or mutations within the cells. In another embodiment, the present invention is used to identify aptamers that bind intracellular ligands present in differentiated cells. For example, the methods of the present invention may be used to identify ligands or aptamers that bind ligands that are present in induced pluripotent stem cells. In one embodiment, the methods of the present invention can be used to screen for response to cell differentiation in vivo, or physiological changes of cells in vivo.

Aptamer ligands can also be cell endogenous components that increase significantly under specific physiological/pathological conditions, such as oncogenic transformation—these may include second messenger molecules such as GTP or GDP, calcium; fatty acids, or fatty acids that are incorrectly metabolized such as 13-HODE in breast cancer (Flaherty, J T et al., Plos One, Vol. 8, e63076, 2013, incorporated herein by reference); amino acids or amino acid metabolites; metabolites in the glycolysis pathway that usually have higher levels in cancer cells or in normal cells in metabolic diseases; and cancer-associated molecules such as Ras or mutant Ras protein, mutant EGFR in lung cancer, indoleamine-2,3-dioxygenase (IDO) in many types of cancers. Endogenous ligands include progesterone metabolites in breast cancer as disclosed by JP Wiebe (Endocrine-Related Cancer (2006) 13:717-738, incorporated herein by reference). Endogenous ligands also include metabolites with increased levels resulting from mutations in key metabolic enzymes in kidney cancer such as lactate, glutathione, kynurenine as disclosed by Minton, D R and Nanus, D M (Nature Reviews, Urology, Vol. 12, 2005, incorporated herein by reference).

The specificity of the binding of an aptamer to a ligand can be defined in terms of the comparative dissociation constants (Kd) of the aptamer for its ligand as compared to the dissociation constant of the aptamer for unrelated molecules. Thus, the ligand is a molecule that binds to the aptamer with greater affinity than to unrelated material. Typically, the Kd for the aptamer with respect to its ligand will be at least about 10-fold less than the Kd for the aptamer with unrelated molecules. In other embodiments, the Kd will be at least about 20-fold less, at least about 50-fold less, at least about 100-fold less, and at least about 200-fold less. An aptamer will typically be between about 15 and about 200 nucleotides in length. More commonly, an aptamer will be between about 30 and about 100 nucleotides in length.

The aptamers that can be incorporated as part of the riboswitch and screened by methods of the present invention can be a naturally occurring aptamer, or modifications thereof, or aptamers that are designed de novo or synthetic screened through systemic evolution of ligands by exponential enrichment (SELEX). Examples of aptamers that bind small molecule ligands include, but are not limited to theophylline, dopamine, sulforhodamine B, and cellobiose kanamycin A, lividomycin, tobramycin, neomycin B, viomycin, chloramphenicol, streptomycin, cytokines, cell surface molecules, and metabolites. For a review of aptamers that recognize small molecules, see, e.g., Famulok, Science 9:324-9 (1999) and McKeague, M. & DeRosa, M. C. J. Nuc. Aci. 2012. In another embodiment, the aptamer is a complementary polynucleotide.

In one embodiment, the aptamer is prescreened to bind a particular small molecule ligand in vitro. Such methods for designing aptamers include, for example, SELEX. Methods for designing aptamers that selectively bind a small molecule using SELEX are disclosed in, e.g., U.S. Pat. Nos. 5,475,096, 5,270,163, and Abdullah Ozer, et al. Nuc. Aci. 2014, which are incorporated herein by reference. Modifications of the SELEX process are described in U.S. Pat. Nos. 5,580,737 and 5,567,588, which are incorporated herein by reference.

Previous selection techniques for identifying aptamers generally involve preparing a large pool of DNA or RNA molecules of the desired length that contain a region that is randomized or mutagenized. For example, an oligonucleotide pool for aptamer selection might contain a region of 20-100 randomized nucleotides flanked by regions of defined sequence that are about 15-25 nucleotides long and useful for the binding of PCR primers. The oligonucleotide pool is amplified using standard PCR techniques, or other means that allow amplification of selected nucleic acid sequences. The DNA pool may be transcribed in vitro to produce a pool of RNA transcripts when an RNA aptamer is desired. The pool of RNA or DNA oligonucleotides is then subjected to a selection based on their ability to bind specifically to the desired ligand. Selection techniques include, for example, affinity chromatography, although any protocol which will allow selection of nucleic acids based on their ability to bind specifically to another molecule may be used. Selection techniques for identifying aptamers that bind small molecules and function within a cell may involve cell based screening methods. In the case of affinity chromatography, the oligonucleotides are contacted with the target ligand that has been immobilized on a substrate in a column or on magnetic beads. The oligonucleotide is preferably selected for ligand binding in the presence of salt concentrations, temperatures, and other conditions which mimic normal physiological conditions. Oligonucleotides in the pool that bind to the ligand are retained on the column or bead, and nonbinding sequences are washed away. The oligonucleotides that bind the ligand are then amplified (after reverse transcription if RNA transcripts were utilized) by PCR (usually after elution). The selection process is repeated on the selected sequences for a total of about three to ten iterative rounds of the selection procedure. The resulting oligonucleotides are then amplified, cloned, and sequenced using standard procedures to identify the sequences of the oligonucleotides that are capable of binding the target ligand. Once an aptamer sequence has been identified, the aptamer may be further optimized by performing additional rounds of selection starting from a pool of oligonucleotides comprising a mutagenized aptamer sequence.

In one embodiment, the aptamer or aptamer library for use in the present invention comprises one or more aptamers identified in an in vitro aptamer screen. In one embodiment, the aptamers identified in the in vitro aptamer screen have one or more nucleotides randomized to create a prospective aptamer library for use in the methods of the present invention.

The Alternative Exon

The alternative exon that is part of the gene regulation polynucleotide cassette of the present invention can be any polynucleotide sequence capable of being transcribed to a pre-mRNA and alternatively spliced into the mRNA of the target gene. The alternative exon that is part of the gene regulation cassette of the present invention contains at least one sequence that inhibits translation such that when the alternative exon is included in the target gene mRNA, expression of the target gene from that mRNA is prevented or reduced. In a preferred embodiment, the alternative exon contains a stop codon (TGA, TAA, TAG) that is in frame with the target gene when the alternative exon is included in the target gene mRNA by splicing. In embodiments, the alternative exon comprises, in addition to a stop codon, or as an alternative to a stop codon, other sequence that reduces or substantially prevents translation when the alternative exon is incorporated by splicing into the target gene mRNA including, e.g., a microRNA binding site, which leads to degradation of the mRNA. In one embodiment, the alternative exon comprises a miRNA binding sequence that results in degradation of the mRNA. In one embodiment, the alternative exon encodes a polypeptide sequence which reduces the stability of the protein containing this polypeptide sequence. In one embodiment, the alternative exon encodes a polypeptide sequence which directs the protein containing this polypeptide sequence for degradation.

The basal or background level of splicing of the alternative exon can be optimized by altering exon splice enhancer (ESE) sequences and exon splice suppressor (ESS) sequences and/or by introducing ESE or ESS sequences into the alternative exon. Such changes to the sequence of the alternative exon can be accomplished using methods known in the art, including, but not limited to site directed mutagenesis. Alternatively, oligonucleotides of a desired sequence (e.g., comprising all or part of the alternative exon) can be obtained from commercial sources and cloned into the gene regulation cassette. Identification of ESS and ESE sequences can be accomplished by methods known in the art, including, for example using ESEfinder 3.0 (Cartegni, L. et al. ESEfinder: a web resource to identify exonic splicing enhancers. Nucleic Acid Research, 2003, 31(13): 3568-3571) and/or other available resources.

In one embodiment, the alternative exon is exogenous to the target gene, although it may be derived from a sequence originating from the organism where the target gene will be expressed. In one embodiment the alternative exon is a synthetic sequence. In one embodiment, the alternative exon is a naturally-occurring exon. In another embodiment, the alternative exon is derived from all or part of a known exon. In this context, "derived" refers to the alternative exon containing sequence that is substantially homologous to a naturally occurring exon, or a portion thereof, but may contain various mutations, for example, to introduce a stop codon that will be in frame with the target reporter gene sequence, or to introduce or delete an exon splice enhancer, and/or introduce delete an exon splice suppressor. In one embodiment, the alternative exon is derived from exon 2 of the human dihydrofolate reductase gene (DHFR), mutant human Wilms tumor 1 exon 5, mouse calcium/calmodulin-dependent protein kinase II delta exon 16, or SIRT1 exon 6.

5' and 3' Intronic Sequences

The alternative exon is flanked by 5' and 3' intronic sequences. The 5' and 3' intronic sequences that can be used in the gene regulation cassette can be any sequence that can be spliced out of the target gene creating either the target gene mRNA or the target gene comprising the alternative exon in the mRNA, depending upon the presence or absence of a ligand that binds the aptamer. The 5' and 3' introns each has the sequences necessary for splicing to occur, i.e., splice donor, splice acceptor and branch point sequences. In one embodiment, the 5' and 3' intronic sequences of the gene regulation cassette are derived from one or more naturally occurring introns or a portion thereof. In one embodiment, the 5' and 3' intronic sequences are derived from a truncated human beta-globin intron 2 (IVS2Δ). In other embodiments the 5' and 3' intronic sequences are derived from the SV40 mRNA intron (used in pCMV-LacZ vector from Clontech), intron 6 of human triose phosphate isomerase (TPI) gene (Nott Ajit, et al. RNA. 2003, 9:6070617), or an intron from human factor IX (Sumiko Kurachi et al. J. Bio. Chem. 1995, 270(10), 5276), the target gene's own endogenous intron, or any genomic fragment or synthetic introns (Yi Lai, et al. Hum Gene Ther. 2006:17(10):1036) that contain elements that are sufficient for regulated splicing (Thomas A. Cooper, Methods 2005 (37):331).

In one embodiment, the alternative exon and riboswitch of the present invention are engineered to be in an endogenous intron of a target gene. That is, the intron (or substantially similar intronic sequence) naturally occurs at that position of the target gene. In this case, the intronic sequence immediately upstream of the alternative exon is referred to as the 5' intron or 5' intronic sequence, and the intronic sequence immediately downstream of the alternative exon is referred to as the 3' intron or 3' intronic sequence. In this case, the endogenous intron is modified to contain a splice acceptor sequence and splice donor sequence flanking the 5' and 3' ends of the alternative exon.

The splice donor and splice acceptor sites in the gene regulation cassette of the present invention can be modified to be strengthened or weakened. That is, the splice sites can be modified to be closer to the consensus for a splice donor or acceptor by standard cloning methods, site directed mutagenesis, and the like. Splice sites that are more similar to the splice consensus tend to promote splicing and are thus strengthened. Splice sites that are less similar to the splice consensus tend to hinder splicing and are thus weakened. The consensus for the splice donor of the most common class of introns (U2) is A/C A G ∥ G T A/G A G T (where ∥ denotes the exon/intron boundary). The consensus for the splice acceptor is C A G ∥ G (where ∥ denotes the exon/intron boundary). The frequency of particular nucleotides at the splice donor and acceptor sites are described in the art (see, e.g., Zhang, M. Q., Hum Mol Genet. 1988. 7(5):919-932). The strength of 5' and 3' splice sites can be adjusted to modulate splicing of the alternative exon.

Additional modifications to 5' and 3' introns in the gene regulation cassette can be made to modulate splicing including modifying, deleting, and/or adding intronic splicing enhancer elements and/or intronic splicing suppressor elements, and/or modifying the branch site sequence.

In one embodiment, the 5' intron has been modified to contain a stop codon that will be in frame with the reporter gene. The 5' and 3' intronic sequences can also be modified to remove cryptic slice sites, which can be identified with publicly available software (see, e.g., Kapustin, Y. et al. Nucl. Acids Res. 2011. 1-8). The lengths of the 5' and 3' intronic sequences can be adjusted in order to, for example, meet the size requirements for viral expression constructs. In one embodiment, the 5' and 3' intronic sequences are independently from about 50 to about 300 nucleotides in length. In one embodiment, the 5' and 3' intronic sequences are independently from about 125 to about 240 nucleotides in length.

Reporter Genes

The screening methods of the present invention utilize a gene regulation cassette that is used to regulate the expression of a target gene (e.g., a reporter gene) that can be expressed in a target cell, tissue or organism. The reporter gene can be any gene whose expression can be used to detect the specific interaction of a ligand with the aptamer in the gene regulation cassette. In one embodiment, the reporter gene encodes a fluorescent protein, including, e.g., a green fluorescent protein (GFP), a cyan fluorescent protein, a yellow fluorescent protein, an orange fluorescent protein, a red fluorescent protein, or a switchable fluorescent protein. In another embodiment, the reporter gene encodes a luciferase enzyme including, e.g., firefly luciferase, *Renilla* luciferase, or secretory *Gaussia* luciferase. In one embodiment, the reporter gene is β-galactosidase. In one embodiment, the reporter is horseradish peroxidase (HRP). In one embodiment, the reporter gene is selected from the group consisting of a nuclear protein, transporter, cell membrane protein, cytoskeleton protein, receptor, growth hormone, cytokine, signaling molecule, regulatory RNA, antibody, and therapeutic proteins or peptides.

Expression Constructs

The present invention contemplates the use of a recombinant vector for introduction into target cells a polynucleotide encoding a reporter gene and containing the gene regulation cassette of the present invention. In many embodiments, the recombinant DNA construct of this invention includes additional DNA elements including DNA segments that provide for the replication of the DNA in a host cell and expression of the target gene in that cell at appropriate levels. The ordinarily skilled artisan appreciates that expression control sequences (promoters, enhancers, and the like) are selected based on their ability to promote expression of the reporter gene in the target cell. "Vector" means a recombinant plasmid, yeast artificial chromosome (YAC), mini chromosome, DNA mini-circle or virus (including virus derived sequences) that comprises a polynucleotide to be delivered into a host cell, either in vitro or in vivo. In one embodiment, the recombinant vector is a viral vector or a combination of multiple viral vectors. Viral vectors for the aptamer-mediated expression of a reporter gene in a target cell are known in the art and include adenoviral (AV) vectors, adeno-associated virus (AAV) vectors, retroviral and lentiviral vectors, and Herpes simplex type 1 (HSV1) vectors.

Methods for Dividing Aptamer Libraries into Sub-Libraries

Another aspect of the present invention provides methods to divide large oligonucleotide libraries into smaller sub-libraries and approaches to make cellular assay-screenable plasmid libraries of aptamer-based synthetic riboswitches. One aspect of the invention provides a method for splitting an oligonucleotide library into smaller sub-libraries comprising the steps:

(a) providing an oligonucleotide library wherein the oligonucleotides in the library comprise multiple 5' and 3' constant regions, (b) performing a two-cycle PCR using the oligonucleotide library as the template and first primers and second primers that are complementary to the 5' and 3' constant regions,
(c) isolating the products of the two-cycle PCR, and
(d) PCR amplifying a subset of the isolated products of the two-cycle PCR using primers complementary to a subset of the unique 5' and 3' constant regions.

In one embodiment, the oligonucleotide library is a randomized aptamer library containing one or more randomized nucleotides. The aptamer sequences are flanked by a left and right constant region, which contain a restriction site for subsequent cloning.

In one embodiment, the first or second primer in the two-cycle PCR comprises a label selected from the group consisting of biotin, digoxigenin (DIG), bromodeoxyuridine (BrdU), fluorophore, a chemical group, e.g. thiol group, or a chemical group e.g. azides used in Click Chemistry. These molecules can be linked to the oligonucleotides, and their interacting molecules, such as streptavidin or modified forms of avidin for biotin, antibodies against DIG or BrdU or fluorophore, or a second thiol group to form disulfide, alkyne group for azides, can be immobilized on a solid surface to facilitate the isolation of labeled oligonucleotides.

Once an aptamer library is divided into sub-libraries of aptamers, the aptamers in one or more sub-libraries are introduced into the gene regulation polynucleotide cassette to generate a riboswitch library and screened for ligand binding by the methods provided herein.

Methods for Dividing Riboswitch Libraries into Sub-Libraries

In one aspect the present invention provides a method for dividing a library of riboswitches into sub-libraries. A library of riboswitches as used herein is a plasmid library comprising a gene regulation polynucleotide cassette, e.g., as described herein and in PCT/US2016/016234, comprising a plurality of aptamers where individual members of the library comprise aptamer sequences that is different from other members of the library. In embodiments, the aptamers in the library of riboswitches comprise one or more randomized nucleotides. In embodiments, the plasmid riboswitch library was generated from an aptamer sub-library created by the methods described herein.

The method for dividing the riboswitch library into sub-libraries comprises the steps of:
(a) introducing a library of aptamers into a plasmid comprising a gene regulation polynucleotide cassette described herein to make a riboswitch library;
(b) introducing the riboswitch library into bacteria (e.g., E. coli);
(c) collecting bacterial clones (for example by picking bacterial colonies) and extracting plasmid DNA to obtain plasmid sub-libraries of riboswitches (referred to herein as primary sub-libraries);
(d) optionally, generating secondary sub-libraries of riboswitches from a primary plasmid sub-library of riboswitches by introducing a primary sub-library into bacteria, collecting bacterial clones and isolating the plasmid DNA.

Methods for introducing sequences into plasmids to generate a library are known in the art as are methods for introducing plasmids into bacteria and obtaining bacterial clones. Bacterial clones containing a member of the plasmid riboswitch library may be collected by plating bacteria and picking individual colonies. Pooled plasmids from these clones form the sub-library. The number of bacterial clones collected determines the size (number of unique members) of the sub-library of riboswitches and multiple sub-libraries may be generated. One or more primary sub-libraries can be further divided to create secondary sub-libraries to further reduce the size of the sub-libraries. The sub-libraries are screened using the methods described herein by introducing one or more sub-library into eukaryotic cells, exposing the cells to a ligand of interest, and measuring the expression of the reporter gene from the gene regulation polynucleotide cassette. Increase in reporter gene expression in response to ligand indicates that one or more members of the library comprises an aptamer that binds to the ligand in the context of the riboswitch. Thus, the size of the sub-library that can be screened may be determined by the sensitivity of the assay for measuring reporter gene expression. In embodiments of the invention, a sub-library comprises about 50 to about 600 unique members (although some members may be repeated in other sub-libraries).

It is to be understood and expected that variation in the principles of invention herein disclosed can be made one of ordinary skill in the art and it is intended that such modifications are to be included within the scope of the present invention. All references cited herein are hereby incorporated by reference in their entirety. The following examples further illustrate the invention, but should not be construed to limit the scope of the invention.

Example 1

Mammalian Cell-Based Screening for Aptamer/Ligands Using Splicing-Based Gene Regulating Riboswitches.

Procedures:

Construction of Riboswitches:

Riboswitches were constructed as described in PCT/US2016/016234 (in particular Examples 3 to 6), incorporated herein by reference. A truncated human beta-globin intron sequence was synthesized and inserted in the coding sequence of a firefly luciferase gene. A mutant human DHFR exon 2 was synthesized and inserted in the middle of this truncated beta-globin intron sequence using Golden gate cloning strategy. Aptamers including xpt-G/A$^1$, ydhl-G/A$^2$, yxj$^3$, add$^4$, gdg6-G/A$^5$ (citations for the aptamers are incorporated herein by reference) were synthesized as oligonucleotides ("oligos") with 4 nucleotide overhang at the 5' end that are complementary to two different BsaI sites individually (IDT), annealed and ligated to BsaI-digested mDHFR-Luci-acceptor vector.

Transfection:

$3.5 \times 10^4$ HEK 293 cells were plated in a 96-well flat bottom plate the day before transfection. Plasmid DNA (500 ng) was added to a tube or a 96-well U-bottom plate. Separately, TransIT-293 reagent (Mirus; 1.4 µL) was added to 50 µL Opti-mem I media (Life Technologies), and allowed to sit for 5 minutes at room temperature (RT). Then, 50 µL of this diluted transfection reagent was added to the DNA, mixed, and incubated at RT for 20 min. Finally, 7 µL of this solution was added to a well of cells in the 96-well plate.

Firefly Luciferase Assay of Cultured Cells:

24 hours after media change, plates were removed from the incubator, and equilibrated to RT for several minutes on a lab bench, then aspirated. Glo-lysis buffer (Promega, 100 µL, RT) was added, and the plates maintained at RT for at least 5 minutes. Then, the well contents were mixed by 50 µL trituration, and 20 µL of each sample was mixed with 20 µL of bright-glo reagent (Promega) that had been diluted to 10% in glo-lysis buffer. 96 wells were spaced on an opaque white 384-well plate. Following a 5 min incubation at RT, luminescence was measured using a Tecan machine with 500 mSec read time. The luciferase activity was expressed as mean relative light unit (RLU)±S.D., and fold induction was calculated as the luciferase activity obtained with guanine treatment divided by luciferase activity obtained without guanine treatment.

Figure 1B:
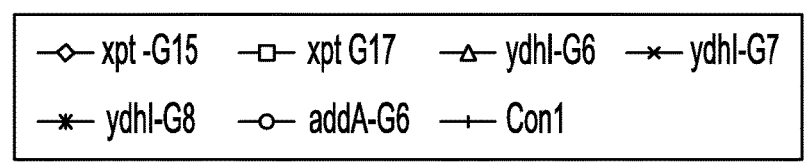
FIG. 1b. Dose responses of constructs with regulatory cassettes containing different aptamer based riboswitches. Guanine riboswitches induced reporter gene expression by responding not only to guanine but also guanosine treatment.
Figure 1B:
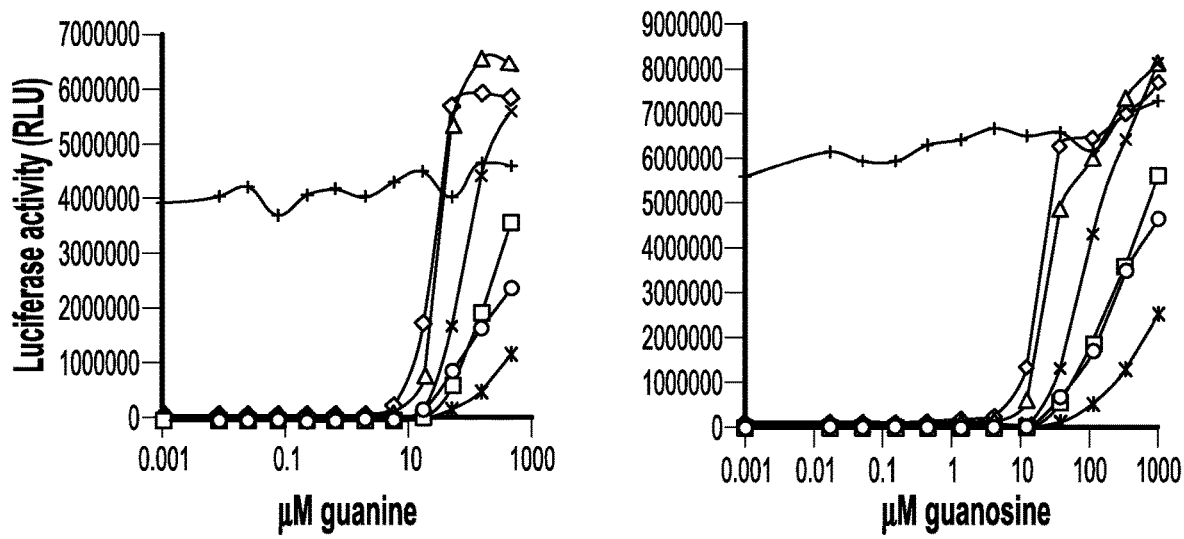

Results:

Starting with luciferase as a reporter gene, a gene expression platform was created by inserting a human β-globin intron in the middle of the coding sequence of firefly luciferase and a mutant stop codon-containing human DHFR exon 2 in the intron portion. The reporter gene expression is thus controlled by the inclusion or exclusion of the mDHFR exon containing a stop codon that is in frame with the reporter gene. In this system, a hairpin structure in the mRNA formed by U1 binding site and an inserted complimentary sequence blocks the inclusion of mDHFR exon, therefore enabling target gene expression (FIG. 1a). To make the formation of hairpin structure regulatable, thus target gene expression controllable by small molecules, we grafted either synthetic aptamers (theophylline) or natural aptamers (xpt-G/A, yxj, ydhl-A/G, add-A/G aptamers) or hybrid aptamer gdg6-G/A) to this splicing-based gene regulation platform in between the U1 binding site and its complementary sequence, and generated synthetic riboswitches that regulate gene expression in mammalian cells. By using our splicing-based gene regulation cassette and inserting different aptamers into our synthetic riboswitch construct, we demonstrated different functional responses to ligand in the context of mammalian cells. Those riboswitches with guanine aptamers responds to guanine as well as guanosine as shown in FIG. 1b. The xpt-guanine riboswitch, xpt-G17 (disclosed in PCT/US2016/016234, see, e.g., SEQ ID NO.:15, incorporated herein by reference), yielded high dynamic range of induction of reporter gene expression in response to ligand with its natural ligand treatment.

Figure 1C:
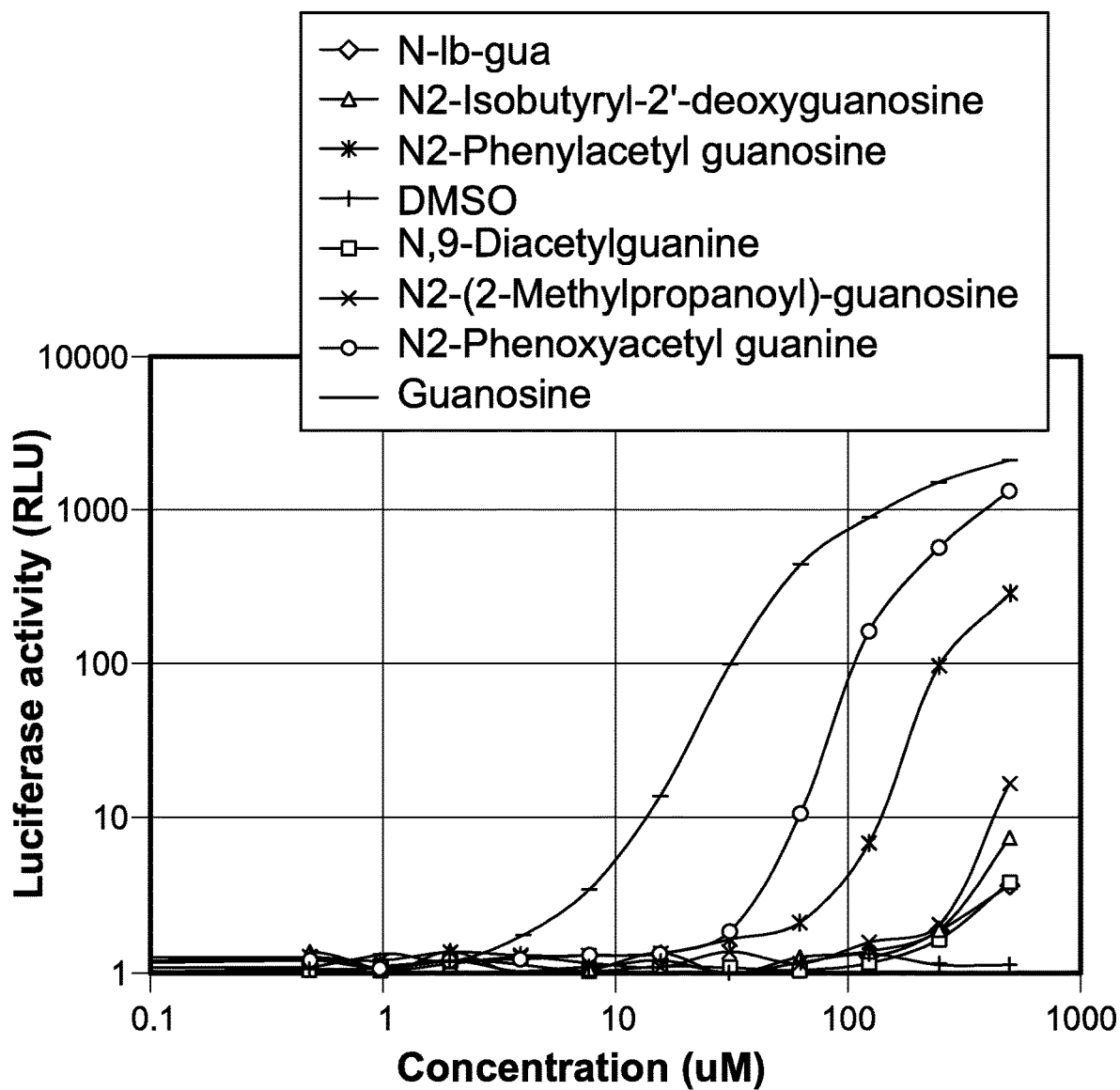
FIGS. 1c and 1d. Graph demonstrating that the xpt-G17 riboswitch induces luciferase activity upon treatment with guanine analogs.
Figure 1D:
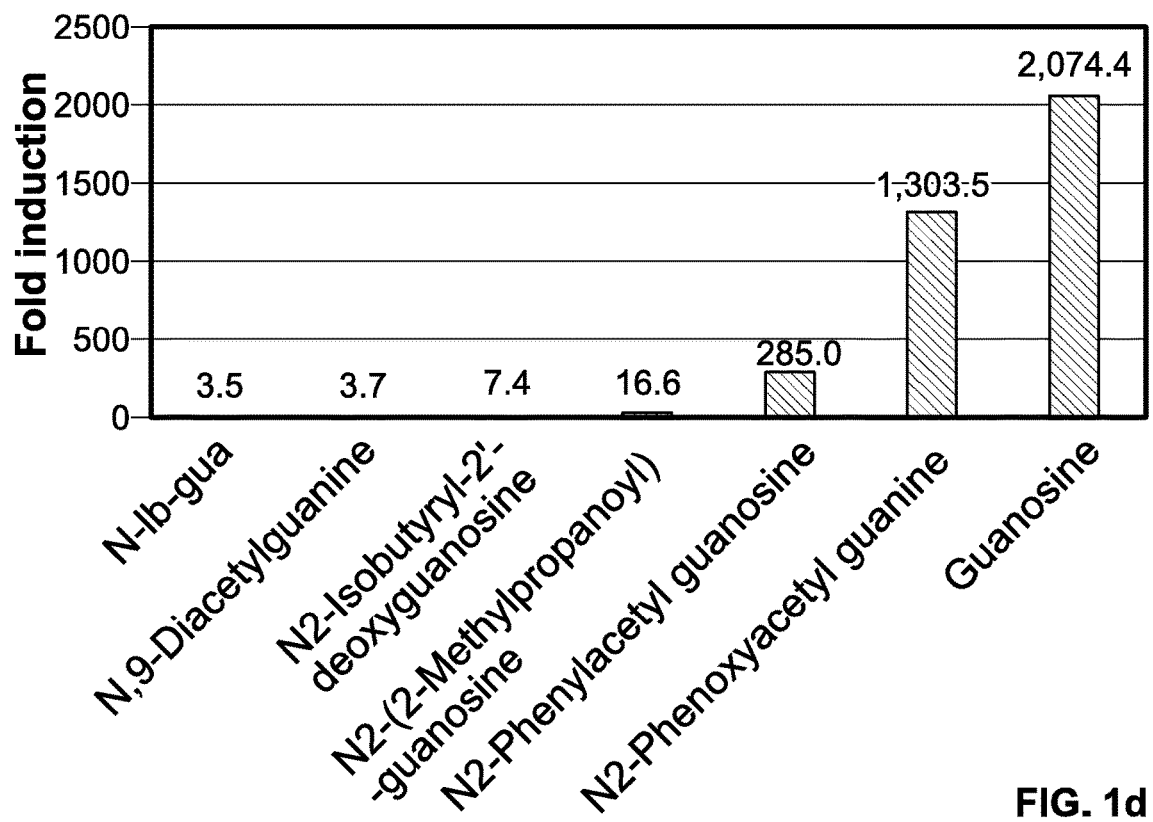
Figure 1E:
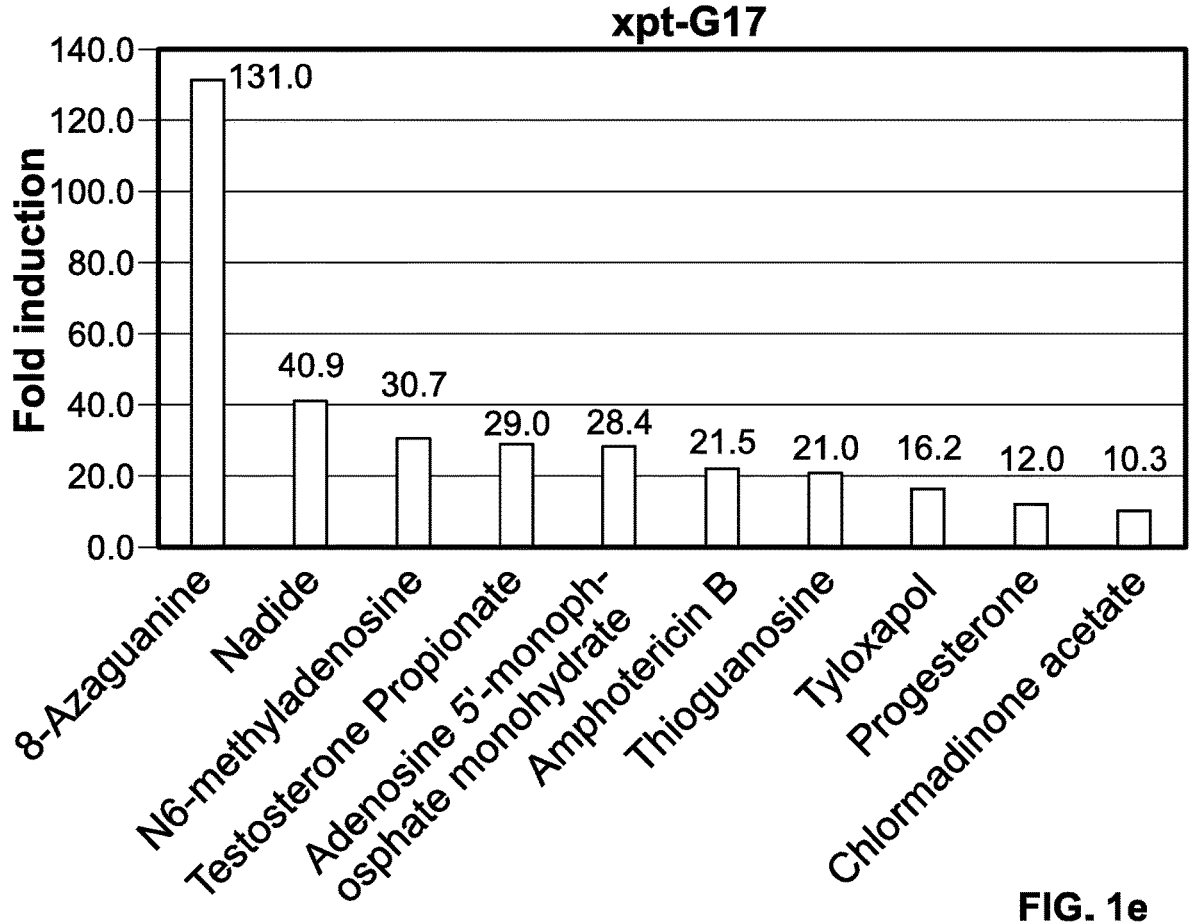
FIG. 1e. Fold induction of luciferase activity by xpt-G17 riboswitch upon treatment with compounds.
Figure 2:
FIG. 2. Schematic of a template for generating randomized aptamer sequences. The aptamer sequence (blank bar) is flanked by constant regions (black bars), which contain BsaI site to facilitate the cloning of aptamer into a gene regulation cassette to generate riboswitches.

Although the natural aptamer-based riboswitches have high dynamic range in regulating gene expression in mammalian cells, the nature of the ligands for those natural aptamers limits their applicability in vivo. Taking advantage of our highly dynamic gene regulation platform with riboswitches, we first chose a list of guanine analogs that have different chemical groups at N2 position to test their activities on xpt-G17 riboswitch. As shown in FIG. 1c, at 500 µM concentration, several N2 compounds induced luciferase activity in cells with xpt-G17 construct, with N2-Phenoxyacetyl guanine being the most potent (1303-fold induction) as shown in FIG. 1d. To expand the list of compounds for use as potential ligands, the Prestwick library (a collection of 1280 clinically approved drugs) was used at 100 µM to screen for optimal ligands to activate known aptamers in the context of mammalian cells. As shown in FIG. 1e from a preliminary screen, the guanine riboswitch xpt-G17 responded not only to guanine, but also to 8-azaguanine, Nadide, N6-methyladenosine, Testosterone propionate, Adenosine 5'-monophosphate monohydrate, amphotericin B, Thioguanine, Tyloxapol, Progesteron and Chlormadinone acetate as shown in FIG. 1e, as well as a number of other compounds as listed in Table 1. Intriguingly, some of these compounds that showed activities on xpt-G17 riboswitch are structurally very different from guanine or guanosine. The Prestwick library was further screened with other 8 purine riboswitches, and a number of compounds that can activate the riboswitches in inducing luciferase activity were obtained (Table 1). These results demonstrate the important usage of the riboswitch system in discovering potential optimal ligands for known aptamer in cellular environment, further highlighting the importance of generating aptamers in the context of the cells within which the riboswitch will be required to function.

TABLE 1

| Riboswitch | Compound name | Fold Induction |
|---|---|---|
| xpt-G17 | 8-Azaguanine | 131.0 |
| xpt-G17 | Azathioprine | 6.2 |
| xpt-G17 | Cinnarizine | 3.5 |
| xpt-G17 | Pimethixene maleate | 4.7 |
| xpt-G17 | N6-methyladenosine | 30.7 |
| xpt-G17 | thioguanosine | 21.0 |
| xpt-G17 | Adenosine 5'-monophosphate monohydrate | 28.4 |
| xpt-G17 | Amphotericin B | 21.5 |
| xpt-G17 | Testosterone propionate | 29.0 |
| xpt-G17 | Haloprogin | 5.1 |
| xpt-G17 | Idebenone | 3.3 |
| xpt-G17 | Zotepine | 4.3 |
| xpt-G17 | Progesterone | 12.0 |
| xpt-G17 | Tenatoprazole | 3.2 |
| xpt-G17 | Acetopromazine maleate salt | 4.5 |
| xpt-G17 | Etofenamate | 7.5 |
| xpt-G17 | Mercaptopurine | 3.6 |
| xpt-G17 | Avermectin B1 | 4.0 |
| xpt-G17 | Promazine hydrochloride | 3.7 |
| xpt-G17 | Nadide | 40.9 |
| xpt-G17 | Trimeprazine tartrate | 4.9 |
| xpt-G17 | Promethazine hydrochloride | 5.3 |
| xpt-G17 | Tyloxapol | 16.2 |
| xpt-G17 | Chlormadinone acetate | 10.3 |
| xpt-G17 | Pyrvinium pamoate | 5.1 |
| gdg6-A8 | 8-Azaguanine | 305.9 |
| gdg6-A8 | Cimetidine | 3.0 |
| gdg6-A8 | Azathioprine | 19.9 |
| gdg6-A8 | Diperodon hydrochloride | 3.0 |
| gdg6-A8 | Pimethixene maleate | 9.2 |
| gdg6-A8 | thioguanosine | 20.1 |
| gdg6-A8 | Acetopromazine maleate salt | 8.6 |
| gdg6-A8 | Mercaptopurine | 17.2 |
| gdg6-A8 | Opipramol dihydrochloride | 3.1 |
| gdg6-A8 | Promazine hydrochloride | 12.6 |
| gdg6-A8 | Methotrimeprazine maleate salt | 5.0 |
| gdg6-A8 | Dienestrol | 4.3 |
| gdg6-A8 | Trimipramine maleate salt | 5.3 |
| gdg6-A8 | Trimeprazine tartrate | 8.7 |
| gdg6-A8 | Promethazine hydrochloride | 4.8 |
| gdg6-A8 | Vorinostat | 6.4 |
| gdg6-A8 | Methiazole | 3.8 |
| yxj-A6 | 8-Azaguanine | 55.6 |
| yxj-A6 | Azathioprine | 6.6 |
| yxj-A6 | Pimethixene maleate | 4.9 |
| yxj-A6 | thioguanosine | 10.2 |
| yxj-A6 | Acetopromazine maleate salt | 3.1 |
| yxj-A6 | Mercaptopurine | 10.0 |
| yxj-A6 | Promazine hydrochloride | 6.6 |
| yxj-A6 | Sulfaquinoxaline sodium | 3.4 |
| yxj-A6 | Trimipramine maleate salt | 3.3 |
| yxj-A6 | Trimeprazine tartrate | 7.0 |
| yxj-A6 | Promethazine hydrochloride | 7.9 |
| yxj-A6 | Pirlindole mesylate | 3.2 |
| add-A6 | 8-Azaguanine | 22.1 |
| add-A6 | Azathioprine | 6.5 |
| add-A6 | Pimethixene maleate | 4.2 |
| add-A6 | thioguanosine | 5.9 |
| add-A6 | Acetopromazine maleate salt | 3.5 |
| add-A6 | Mercaptopurine | 15.0 |
| add-A6 | Opipramol dihydrochloride | 4.3 |
| add-A6 | Promazine hydrochloride | 10.5 |
| add-A6 | Sulfaquinoxaline sodium | 3.3 |
| add-A6 | Terazosin hydrochloride | 3.5 |
| add-A6 | Trimipramine maleate salt | 3.4 |
| add-A6 | Trimeprazine tartrate | 4.0 |
| add-A6 | Promethazine hydrochloride | 4.5 |
| add-A6 | Deptropine citrate | 3.3 |
| add-A6 | Alcuronium chloride | 4.2 |
| ydhl-A6 | Hydrochlorothiazide | 3.3 |
| ydhl-A6 | 8-Azaguanine | 3.7 |

TABLE 1-continued

| Riboswitch | Compound name | Fold Induction |
|---|---|---|
| ydhl-A6 | Ticlopidine hydrochloride | 3.1 |
| ydhl-A6 | Alverine citrate salt | 4.2 |
| ydhl-A6 | Vincamine | 3.3 |
| ydhl-A6 | Idebenone | 3.5 |
| ydhl-A6 | Pepstatin A | 4.0 |
| ydhl-A6 | Modafinil | 3.8 |
| ydhl-A6 | Benperidol | 3.1 |
| ydhl-A6 | Digoxigenin | 4.5 |
| ydhl-A6 | Digoxigenin | 3.3 |
| ydhl-A6 | Moricizine hydrochloride | 10.3 |
| ydhl-A6 | Pivmecillinam hydrochloride | 3.2 |
| ydhl-A6 | Piperidolate hydrochloride | 3.4 |
| ydhl-A6 | Oxaprozin | 3.4 |
| ydhl-A6 | Imidurea | 4.3 |
| ydhl-A6 | Mecamylamine hydrochloride | 3.2 |
| xpt-A8 | 8-Azaguanine | 95.1 |
| xpt-A8 | Azathioprine | 5.9 |
| xpt-A8 | Pimethixene maleate | 3.3 |
| xpt-A8 | thioguanosine | 11.8 |
| xpt-A8 | Mercaptopurine | 3.4 |
| xpt-A8 | Promazine hydrochloride | 4.1 |
| xpt-A8 | Promethazine hydrochloride | 5.4 |
| gdg6-G8 | 8-Azaguanine | 42.3 |
| gdg6-G8 | Azathioprine | 16.2 |
| gdg6-G8 | Pimethixene maleate | 5.1 |
| gdg6-G8 | thioguanosine | 15.9 |
| gdg6-G8 | Amphotericin B | 3.8 |
| gdg6-G8 | Acetopromazine maleate salt | 3.2 |
| gdg6-G8 | Mercaptopurine | 16.2 |
| gdg6-G8 | Promazine hydrochloride | 6.2 |
| gdg6-G8 | Trimipramine maleate salt | 3.3 |
| gdg6-G8 | Trimeprazine tartrate | 6.2 |
| gdg6-G8 | Promethazine hydrochloride | 6.5 |
| gdg6-G8 | Penbutolol sulfate | 3.3 |
| gdg6-G8 | Vorinostat | 10.2 |
| gdg6-G8 | Methiazole | 3.3 |
| gdg6-G8 | Estriol | 4.3 |
| add-G6 | 8-Azaguanine | 47.9 |
| add-G6 | Niclosamide | 3.0 |
| add-G6 | Azathioprine | 11.4 |
| add-G6 | Lynestrenol | 3.8 |
| add-G6 | R(−)Apomorphine hydrochloride hemihydrate | 3.4 |
| add-G6 | Danazol | 3.7 |
| add-G6 | Camptothecine (S, +) | 5.7 |
| add-G6 | Cinnarizine | 3.6 |
| add-G6 | Pimethixene maleate | 6.6 |
| add-G6 | Flunarizine dihydrochloride | 4.7 |
| add-G6 | N6-methyladenosine | 20.8 |
| add-G6 | thioguanosine | 7.9 |
| add-G6 | Adenosine 5'-monophosphate monohydrate | 9.4 |
| add-G6 | Bepridil hydrochloride | 4.4 |
| add-G6 | Amphotericin B | 10.7 |
| add-G6 | Testosterone propionate | 8.8 |
| add-G6 | Haloprogin | 5.9 |
| add-G6 | Idebenone | 6.7 |
| add-G6 | Meclocycline sulfosalicylate | 3.4 |
| add-G6 | Progesterone | 6.0 |
| add-G6 | Acetopromazine maleate salt | 5.0 |
| add-G6 | Etofenamate | 5.1 |
| add-G6 | Mercaptopurine | 14.3 |
| add-G6 | Benzamil hydrochloride | 3.0 |
| add-G6 | Avermectin B1 | 11.8 |
| add-G6 | Promazine hydrochloride | 5.4 |
| add-G6 | Nadide | 30.8 |
| add-G6 | Trimipramine maleate salt | 3.4 |
| add-G6 | Trimeprazine tartrate | 6.2 |
| add-G6 | Simvastatin | 6.2 |
| add-G6 | Promethazine hydrochloride | 6.7 |
| add-G6 | Protriptyline hydrochloride | 5.0 |
| add-G6 | Chlormadinone acetate | 26.1 |
| add-G6 | Nomegestrol acetate | 3.5 |
| add-G6 | Pyrvinium pamoate | 15.8 |
| add-G6 | Sertaconazole Nitrate | 6.5 |
| add-G6 | Vorinostat | 3.6 |
| ydhl-G8 | Sulfaguanidine | 13.9 |
| ydhl-G8 | 8-Azaguanine | 35.6 |
| ydhl-G8 | N6-methyladenosine | 10.7 |
| ydhl-G8 | thioguanosine | 7.5 |
| ydhl-G8 | Adenosine 5'-monophosphate monohydrate | 5.9 |
| ydhl-G8 | Amphotericin B | 6.5 |
| ydhl-G8 | Tetracaine hydrochloride | 3.6 |
| ydhl-G8 | Acetopromazine maleate salt | 3.9 |
| ydhl-G8 | Azelastine hydrochloride | 3.0 |
| ydhl-G8 | Etofenamate | 4.8 |
| ydhl-G8 | Mercaptopurine | 3.6 |
| ydhl-G8 | Promazine hydrochloride | 5.2 |
| ydhl-G8 | Nadide | 11.7 |
| ydhl-G8 | Trimeprazine tartrate | 5.0 |
| ydhl-G8 | Chlormadinone acetate | 10.4 |
| ydhl-G8 | Pyrvinium pamoate | 5.5 |
| ydhl-G8 | Vorinostat | 3.0 |

Sequences for riboswitches used in the Prestwick library screen are provided below with the stem sequences in capital letters, and the aptamer sequences in lowercase letters:

xpt-A8 (SEQ ID NO: 1):
GTAATGTataatcgcgtggatatggcacgcaagtttctaccgggcaccgt aaatgtccgattACATTAC add-G6 (SEQ ID NO: 2):
GTAATGTgtataatcctaatgatatggtttgggagtttctaccaagagcc ttaaactcttgactaCACATTAC add-A6 (SEQ ID NO: 3):
GTAATGTgtataatcctaatgatatggtttgggagtttctaccaagagcc ttaaactcttgattaCACATTAC gdg6-A8 (SEQ ID NO: 4):
GTAATGTacagggtagcataatgggctactgaccccgccgggaaacctat ttcccgattACATTAC gdg6-G8 (SEQ ID NO: 5):
GTAATGTacagggtagcataatgggctactgaccccgccgggaaacctat ttcccgactACATTAC Ydhl-G8 (SEQ ID NO: 6):
GTAATGTataaccctcaataatatggtttgagggtgtctaccaggaaccgt aaaatcctgactACATTAC Ydhl-A6 (SEQ ID NO: 7):
GTAATGTgtataacctcaataatatggtttgagggtgtctaccaggaacc gtaaaatcctgattaCACATTAC yxj-A6 (SEQ ID NO: 8):
GTAATGTgtatatgatcagtaatatggtctgattgtttctacctagtaac cgtaaaaaactagattaCACATTAC Example 2

Design and Synthesis of Aptamer Library.
Procedure

To generate an aptamer library, nucleotides at positions in the aptamer that are identified from crystal structure[6, 7] as potentially involved in ligand binding were randomized. In order to facilitate constructing aptamers into riboswitches, the aptamer region was flanked by constant regions with type IIs restriction enzyme (e.g. BsaI) cut sites. This 153 bp ultramer oligonucleotides containing the aptamer sequence with randomized bases were synthesized by IDT:

```
                                                 (SEQ ID NO: 9)
GACTTCGGTCTCATCCAGAGAATGAAAAAAAAATCTTCAGTAGAAGGT

AATGTATANNNGCGTGGATATGGCACGCNNGNNNNCNCCGGGCACCGT

AAATGTCCGACTACATTACGCACCATTCTAAAGAATAACAGTGAAGAG

ACCAGACGG (N representsrandom nucleotides).
```

To generate more sequence diversity in the aptamer library, bases at more positions can be randomized A completely random sequence can also be used to generate the aptamer library.

Results

As described in Example 1, we have successfully built synthetic riboswitches that regulate mammalian gene expression in responding to small molecule ligand treatment. One of the riboswitches xpt-G17 that contains xpt-G guanine aptamer in the splicing-based gene expression cassette. Using luciferase as a reporter gene, we achieved a high dynamic range of gene regulation in response to guanine treatment, with induction fold of 2000 at high concentration of guanine. This unprecedented dynamic range of gene regulation activity by the aptamer/ligand mediated alternative splicing constructs provides a system to screen for aptamers against a desired ligand in mammalian cells, or screen for ligands which bind and activate known aptamers.

The xpt-G17 was selected as a platform to build a starting riboswitch library. The configuration of oligonucleotide sequence was designed to replace the original xpt-G guanine aptamer in the following cloning steps. The nucleotides in the xpt-G guanine aptamer at positions that are known to be critical for guanine binding based on crystallography analysis were randomized Initially, 10 positions were randomized, which generated a library of 1,048,576 aptamer sequences. When more than 10 positions are randomized, libraries larger than $10^6$ sequences can be generated. Though xpt-G guanine aptamer backbone sequence was used here selectively to randomize, a similar approach can be used to generate aptamer libraries with other known aptamers, or even completely random sequences without known ligands. Though we chose xpt-G17 as platform here, it is important to note that riboswitches with different aptamers, or riboswitches based on mechanisms other than splicing can also be used as a starting platform to generate randomized aptamer sequences.

Example 3

Splitting Large Randomized Aptamer Library into Smaller Sub-Libraries of Aptamer.

Procedures

Oligonucleotides (oligos): JF or JR set of primers have 3' portion sequence complementary to constant regions in the synthesized aptamer oligos and 5' portion sequence containing random 20 mer oligo sequences. F or R set of primers are complimentary to the random 20 mer oligo sequences in the JF or JR primers. All the primers are synthesized at IDT. The JF primers were labeled with biotin at 5' end (IDT). Synthesized oligos were suspended in DNase and RNase-free water to 100 µM as stock solution, and diluted to desired concentration and quantified using Nanodrop machine or OliGreen method (ThermoFisher).

Two-cycle PCR amplification: To add biotinylated oligo-tag, two-cycle PCR amplification was performed using Pfx Platinum PCR kit following manufacturer's protocol in a reaction volume of 10 µl. The oligo templates were used at desired copy numbers in PCR reaction (1 to 5 copies per oligo sequence in the aptamer library). For the first cycle of amplification, only reverse primers JR were included. The amplification was run at 94° C. for 2 minutes, then 94° C. for 10 seconds, annealing with a touch-down program from 66° C. to 52° C. descending at 0.5° C. per minute. Then the polymerase reaction was extended at 68° C. for 20 second followed by cooling down to 4° C. Then 10 µl of PCR mixture without template but containing biotinylated forward primers (biotin-JF) were added to the first cycle PCR tube for the second cycle of amplification using the same PCR steps. The PCR products were ready for incubating with streptavidin-beads.

Isolation of biotinylated oligonucleotides (oligos): 2× Binding and Washing buffer (BW buffer) was made of 1×TE buffer (Ambion) with 2M NaCl. Dynabeads M-270 Streptavidin (ThermoFisher) (SA-beads) was blocked with 20 µM yeast tRNA solution (Ambion) for 10 minutes at room temperature, and washed with 1×BW buffer twice, and re-suspended in the same volume of 2×BW buffer as the initial volume of beads used. 50 µl of these treated beads were added to the PCR products together with 100 µl of 2×BW buffer and 30 µl of water. The 200 µl of biotinylated oligos and SA-beads mixture was incubated at room temperature for 60 minutes, then beads were denatured at 95° C. for 5 minutes, chilled immediately on ice and washed once with 1×BW buffer, twice with water for 5 minutes following manufacturer's protocol. Washing solution was removed as much as possible, and the washed beads were ready for PCR reaction.

Oligo sequence tag-specific PCRs: Beads with biotinylated PCR products were added to a total 50 µl of PCR mix using Pfx Platinum PCR kit. The primers are a mixture of F and R set primers. The PCR was preheated at 94° C. for 2 minutes, subject to 28 cycles of 94° C. for 15 seconds, 62° C. for 30 seconds, 68° C. for 20 seconds, and an additional extension at 68° C. for 2 min. The PCR product was cooled to 12° C. and ready for second round of PCR. For the second round of PCR amplification, 1 µl of the PCR product from the first round of PCR was used as template, and a single pair of F and R primers were used to amplify templates tagged with the complementary sequences. The PCR reaction was preheated at 94° C., and amplified with 25 cycles of 94° C. for 15 seconds, 60° C. for 30 seconds, 68° C. for 20 seconds, and an additional extension at 68° C. for 2 minutes.

Results

Although in vitro selection using systematic evolution of ligands by exponential enrichment (SELEX)[8, 9] has been extensively applied to screening large aptamer libraries usually with $10^{13}$ to $10^{14}$ sequences for generating numerous aptamers against a wide range of ligands including metabolites, vitamin cofactors, metal ions, proteins and even whole cells[10], methods for cell-based screens of such large randomized aptamer libraries have not been developed. Moreover, few aptamers generated by SELEX have proved effective in a cellular environment, highlighting the importance of screening aptamers in the cellular environment where they will be required to function. In order for selected aptamers to work within cells, the binding of the specific aptamer to its ligand must have a functional consequence—which cannot be tested via SELEX, which selects aptamers only based on ligand binding under in vitro conditions. One challenge of developing mammalian cell-based screens for aptamers is the low dynamic gene regulatory range of aptamer-based riboswitches in responding to ligand treatment. In addition to this fundamental limitation, the intrinsic low gene transduction efficiency in mammalian cells imposes another barrier to screening libraries bigger than $10^5$ sequences. However, we developed synthetic riboswitches that can generate up to several thousand-fold induction of gene expression upon ligand treatment. This high dynamic range of gene regulation provides the basis of a cell-based system for screening aptamer/ligands. In order to select aptamers in eukaryotic cells from large aptamer libraries that have high sequence diversity, present invention provides multiple strategies and approaches to divide/split large aptamer libraries to smaller sub-libraries that can be cloned into riboswitch cassette to generate plasmid libraries that are screenable through mammalian cell-based assays.

Figure 3A:
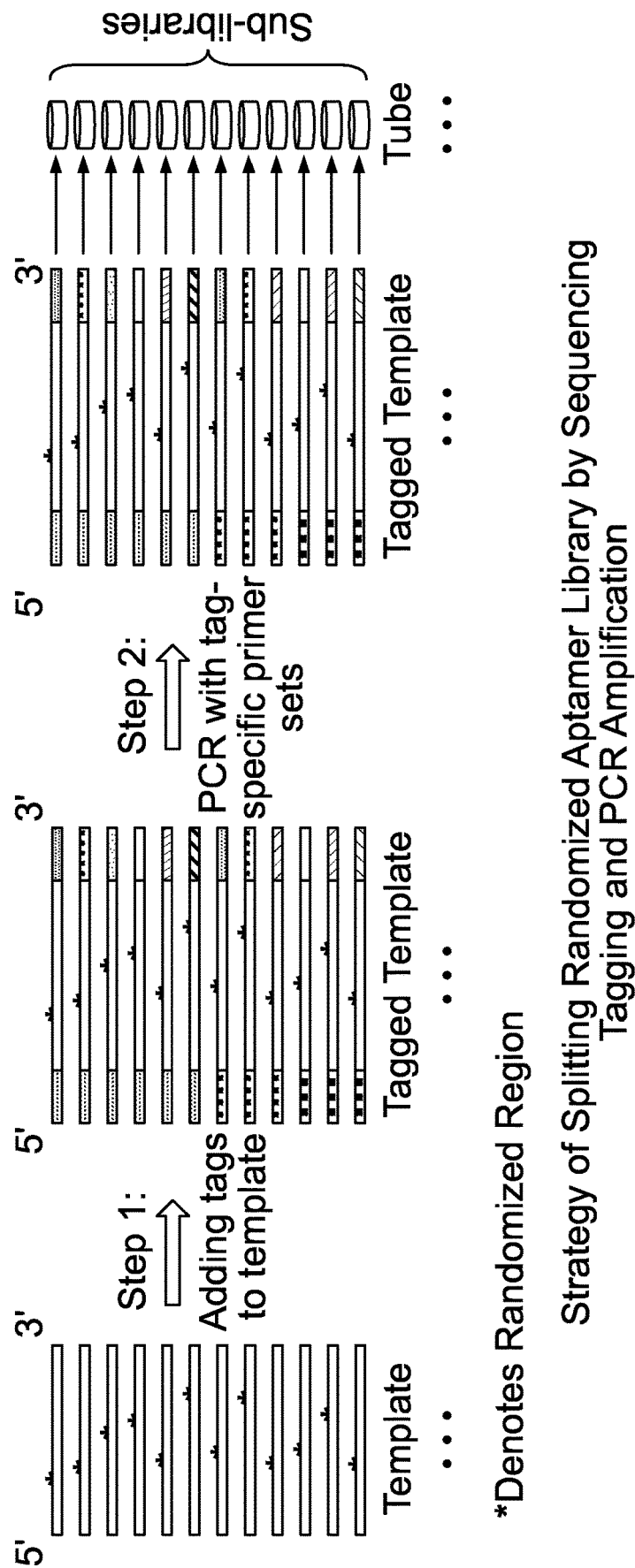
FIGS. 3a to 3e. Schematic description of the method for splitting large randomized aptamer library to smaller sub-libraries.

The strategy of splitting large aptamer libraries is to first add a pair of unique sequences at both the 5' and 3' ends of the synthesized, randomized aptamer oligo sequences (as described in Example 2). In the second step of this strategy, aptamer sequences attached (tagged/labeled) with unique oligo sequences can be amplified using single pair of primers complementary to each pair of sequence tags, thus generating different sub-libraries of aptamers (FIG. 3a). This two-step process of tagging and PCR can be iterated to split the library to the desired sizes.

Figure 3B:
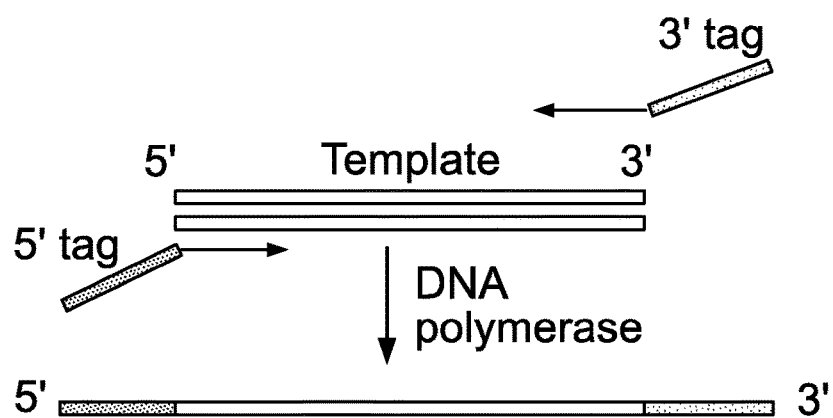
Figure 3B:
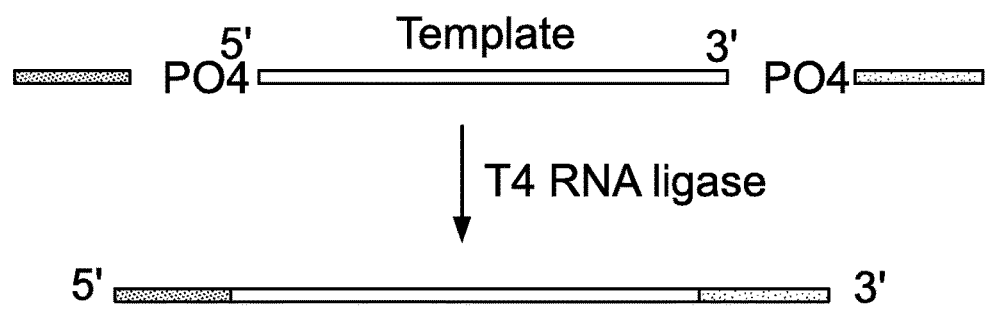
Figure 3B:
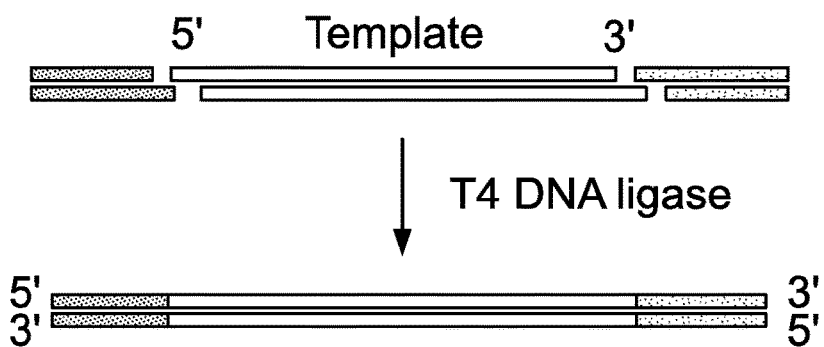

To attach unique sequence pairs to the template, we have developed multiple approaches (FIG. 3b). One approach is to use PCR to incorporate unique sequences to templates (PCR approach). Other approaches include ligating single-strand sequence tag to single-strand template using T4 RNA ligase and ligating by T4 DNA ligase double-strand sequence tags to double-strand templates which are generated by PCR amplification of single-strand oligonucleotide templates (ligation approach). We have developed and tested a two-cycle PCR approach (FIG. 3c), and currently are in a process of testing the ligation approaches to adding unique sequences tags.

Figure 3C:
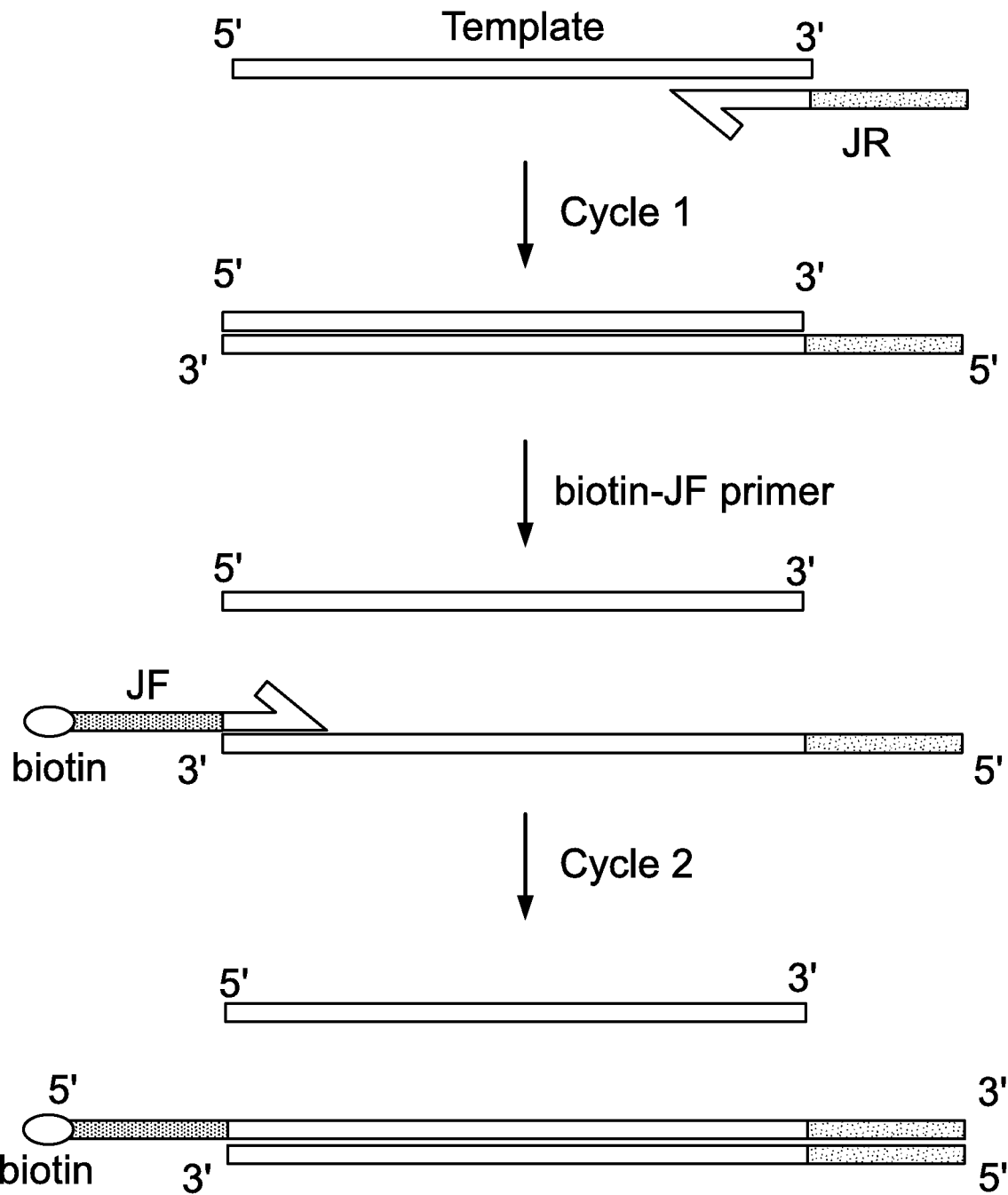
Figure 3D:
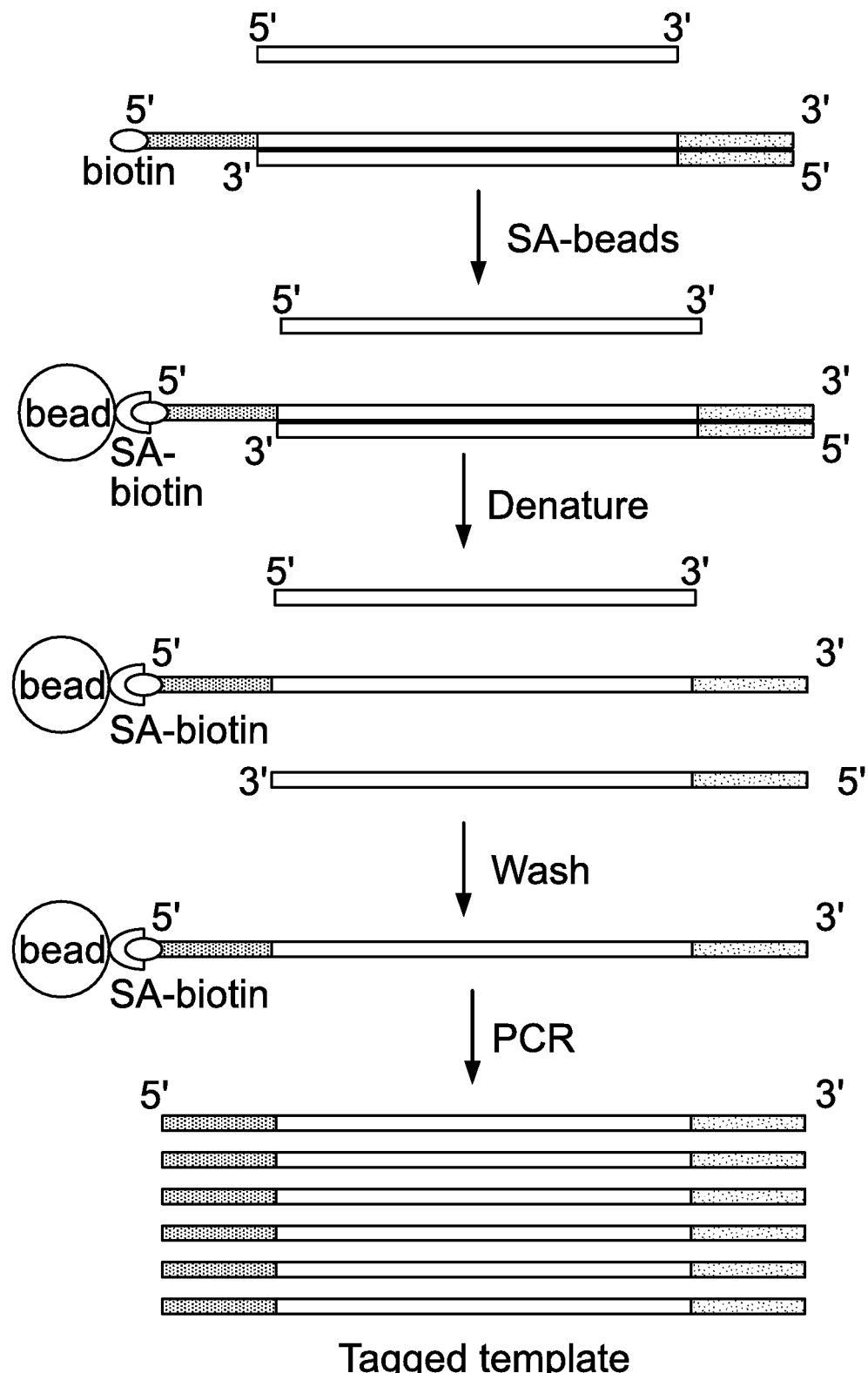

For using PCR approach to attach sequence tags to generate tagged library of aptamer, one set of PCR primers (JF and JR) was designed. This set of primers contains the tag sequence in the 5' portion of the primers, and in the 3' portion of primers, the sequence that is complementary to the constant region in the synthesized aptamer oligos. In order to avoid the heterogeneity generated by multi-cycle conventional PCR[11] using high copy numbers of templates, a two-cycle PCR was developed to attach sequence tag at one end of the template at each cycle (FIG. 3c). In this two-cycle PCR, the copy number of the randomized oligo templates was kept minimum to decrease the chance for each template to be attached with more than one pair of tag sequences. In order to isolate and purify the tagged templates, we labeled JF primers with biotin molecules, so that magnetic streptavidin beads can be used to separate biotinylated tagged templates from the rest of the reaction components (FIG. 3d). Due to the low copy number of templates we started with the PCR tagging, the isolated biotinylated, tagged templates were amplified and expanded by PCR using a mixture of a set of primers (J and F primers) that are specific to the tag sequences attached to the templates, generating the library of aptamers that have unique pair of sequences at the ends (tagged library of randomized aptamers). This PCR product then serves as template for PCR with a single pair of J and R primers to amplify each tagged template, thus generating the sub-libraries of the original aptamer library.

Figure 3E:
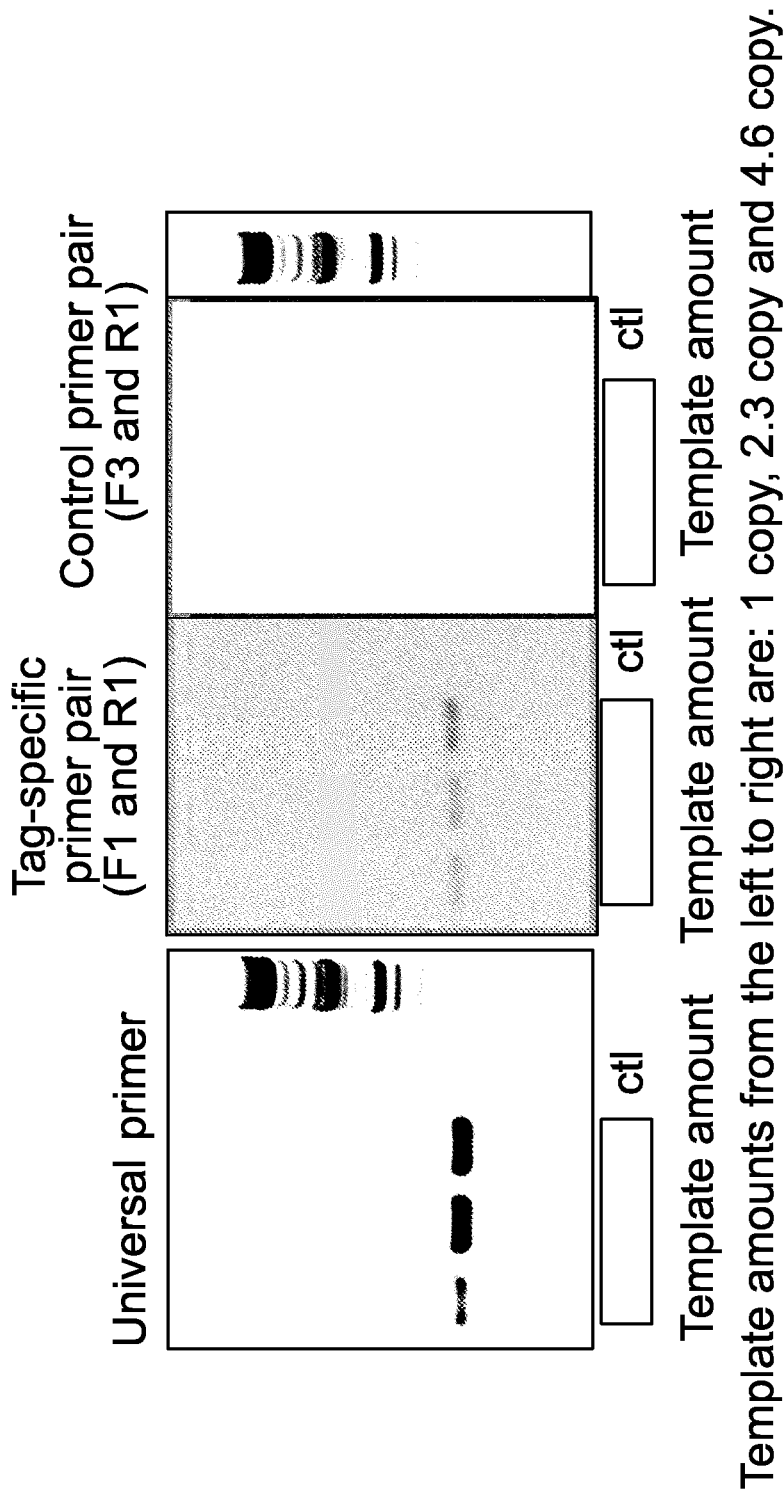
Figure 4:
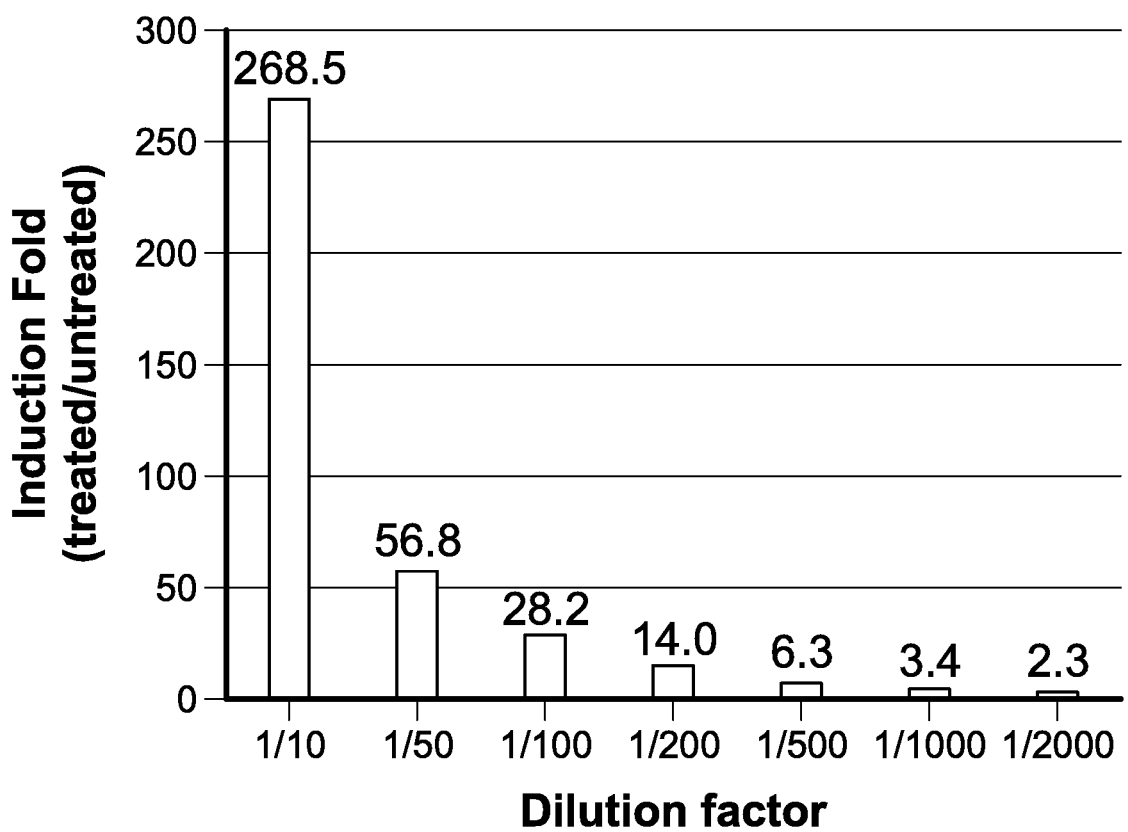
FIG. 4. Sensitivity test on cell-based assay for riboswitch library screening. Construct xpt-G17 was mixed with construct SR-mut at different molecular ratios, and the mixed construct DNA was transfected into HEK-293 cells and treated with guanine. The fold induction of luciferase activity was calculated as luciferase activity induced with guanine divided by luciferase activity obtained without guanine treatment.

In a pilot study where 2 biotin-labeled JF primers (JF1 and JF2) and 8 reverse JR primers (JR1 to JR8) were used, resulting in total 16 unique pairs of sequence tags. After generating the tagged library by PCR with templates at 1, 2.3 or 4.6 copies representing 63%, 90% or 99% of the initial randomized aptamer library, respectively, different primers were used to test the splitting strategy. As shown on the left panel of FIG. 3e, the tagged-templates were amplified by primers complementary to the constant region (universal primers) in the aptamer, which amplify every template in the library. When a single pair of primers (F1 and R1) that are specific to the tag sequences added (middle panel), but not the pair of primers (F3 and R1) which was not included in the tagging (right panel) were used, the tagged-templates were amplified at much lower amount compared to the product amplified with universal primer, indicating only a portion (1/16) of the library was amplified. Thus, the original library was split to smaller sub-libraries.

Example 4

The Sensitivity of Cell-Based Assay for Library Screening.

Procedures:

DNA Constructs:

Plasmid DNA constructs containing xpt-G17 riboswitch was diluted in DNA construct SR-Mut to different ratio of these two DNA constructs. The mixed constructs G17 and SR-mut plasmids DNA were then transfected to HEK 293 cells. Transfection and luciferase assay were performed as described in Example 1.

Results:

The sensitivity of cell-based assay for library screening determines how complex or how big the size of aptamer-riboswitch plasmid library can be in order for minimum 1 positive hit to stand out from the rest of the library in the screen. The assay can be for luciferase activity, fluorescence intensity of fluorescent protein or growth hormone/cytokine release, depending on the reporter gene chosen, and genetic elements can be delivered either by transient transfection or by viral transduction, e.g. AAV, Adeno Virus, lentivirus etc.

Here, we chose transient transfection to deliver plasmid DNA, and used firefly luciferase as reporter gene using xpt-G17 construct as positive riboswitch control vector, an assay that has been extensively tested and used during the development of xpt-G17 riboswitch in mammalian cells. Construct SR-mut was used as negative control vector which has the same genetic elements as xpt-G17 construct except that there is no guanine aptamer sequence, therefore does not activate gene expression in response to guanine treatment. These two constructs were mixed together to mimic a pooled library situation, though the actual riboswitch library is more complex due to the large molecular diversity generated by nucleotide randomization. Cells transfected with 100% xpt-G17 construct DNA yielded 2000-fold induction of luciferase activity upon treatment with 500 µM of guanine when compared to untreated cells. When xpt-G17 construct DNA was diluted with SR-mut construct DNA, cells transfected with the mixed DNA showed lower fold induction of luciferase activity. As shown in FIG. 3, the fold induction decreased when the ratio of guanine responding xpt-G17 construct to non-responding negative SR-mut construct decreased, but still can generate a 2.3-fold induction when there is 1 positive construct out of 2000 molecules, indicating the probability of recovering 1 ligand-responding riboswitch from a mixture of ligand-nonresponding riboswitches.

For assays other than the above described one, the sensitivities of the assay should be tested to provide guidance for determining the size of the sub-library pools to be screened.

Example 5

Construction of Pooled Aptamer-Based Riboswitch Plasmid Library and Splitting of Larger Riboswitch Library to Smaller Screenable Sub-Libraries.

Procedures:

Construction of pooled plasmid library of riboswitches: Ultramer Oligos containing aptamer sequences with randomized bases (see Example 2 for sequence design and composition) were PCR amplified using Platinum Pfx kit (Invitrogen) to generate double stranded DNA fragments, and the generated PCR product was run on 4% agarose gel. The DNA with 153 bp size was gel-purified (Qiagen) and digested with BsaI enzyme (NEB). The BsaI-digested DNA fragment was then ligated to BsaI-digested acceptor vector (mDHFR-Luci-Acceptor) as described in Example 1 with a 1:5 ratio of vector to insert using a T4 DNA ligase (Roche). ElectroMAX DH5α-E competent cells were transformed following the manufacturer's instructions (Invitrogen) with the ligation product and plated onto agar plates. Bacterial colonies were pooled and collected, and DNA was extracted to obtain plasmid library of riboswitches (P1).

A similar approach was used to generate a smaller plasmid riboswitch library (P2) in which nucleotide bases at 5 positions in the aptamer were randomized generating a total of 1024 different aptamer sequences (where N denotes a randomized position):

(SEQ ID NO: 10)
GACTTCGGTCTCATCCAGAGAATGAAAAAAAAATCTTCAGTAGAAGG

TAATGTATANNNGCGTGGATATGGCACGCNNGTTTCTACCGGGCACC

GTAAATGTCCGACTACATTACGCACCATTCTAAAGAATAACAGTGAA

GAGACCAGACGG

Transformation of Chemically Competent DH5α:

227 pg of plasmid DNA was used to transform 50 µl of competent cells to obtain 1:10 ratio of plasmid DNA and bacterial cells. The transformed cells were plated onto agar plates after being incubated at 37° C. without shaking for 30 minutes, and colonies were pooled and collected for DNA extraction using 96-format miniprep kit (Qiagen) to obtain pooled plasmid sub-libraries of riboswitches.

Next Generation Sequencing (NGS):

The plasmid DNA from secondary or tertiary riboswitch sub-libraries was used as templates, and the following primers were used to generate PCR amplicons that contain the randomized aptamer sequences:

DHFR_F:
(SEQ ID NO: 11)
5'-GACTTCGGTCTCATCCAGAGAATGAAAAAAAAATCTTCAGTAGAA

GGTAATG-3';

IVS_R:
(SEQ ID NO: 12)
5'-CCGTCTGGTCTCTTCACTGTTATTCTTTAGAATGGTGCG-3'.

PCR products were subject to NGS using Illumina MiSeq 2×150 bp paired-end platform to generate approximately 700K reads for each sample and subsequent bioinformatics analysis for unique sequence identification and relative abundance calculation (Service provided by Genewiz). Sequences that showed 12, or more than 12, reads from a sequencing run are considered true sequences.

Results

Figure 5A:
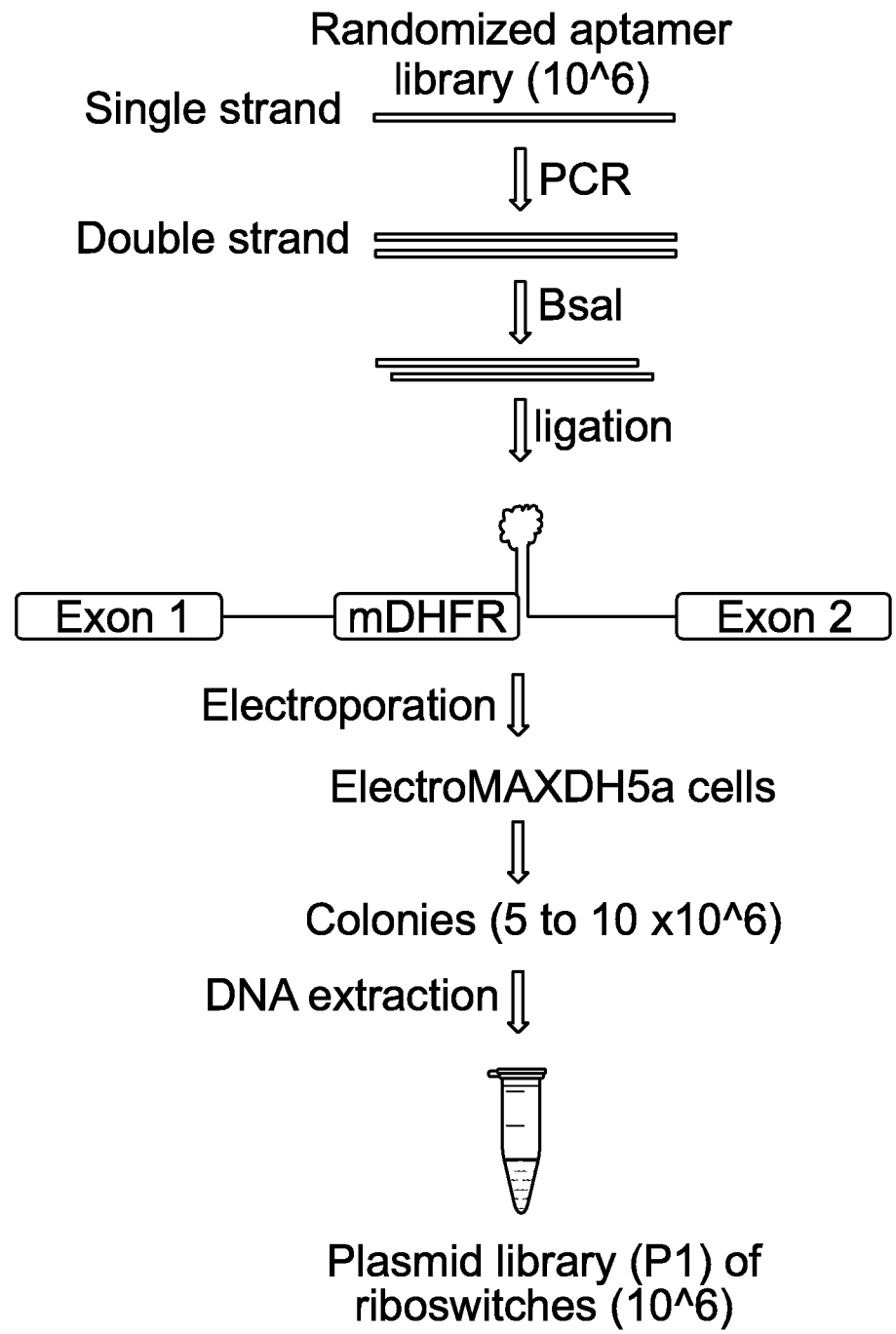
FIG. 5a. Schematic diagram of construction of a plasmid library containing riboswitch. The single stranded aptamer oligos are first PCR amplified using universal primers to convert single stranded aptamer template to double stranded. The double stranded oligos are then digested with BsaI and ligated to BsaI-digested vector to generate constructs with riboswitches. The plasmid DNA is then electroporated into electro-competent DH5a cells. More than $5 \times 10^6$ colonies are collected to cover more than 99% of the initial aptamer library ($10^6$).

To screen aptamers by a cell-based assay, a plasmid library of riboswitches was generated by cloning the aptamer library into mDHFR-Luci-Acceptor vector (FIG. 5a). The constructs generated contain the same configuration of genetic element as in construct xpt-G17, with the only difference being in the aptamer sequences. We started with an aptamer library generated as described in Example 2, a randomized aptamer library comprising of $10^6$ unique sequences. To ensure greater than 99.9% representation of the initial aptamer library, a total of $7.5×10^6$ colonies, which is 7.5 times the number of sequences in the aptamer library, were collected from agar plates. The plasmid DNA extracted from the collected colonies forms the plasmid library (P1) consisting of $10^6$ unique riboswitches.

Figure 5B:
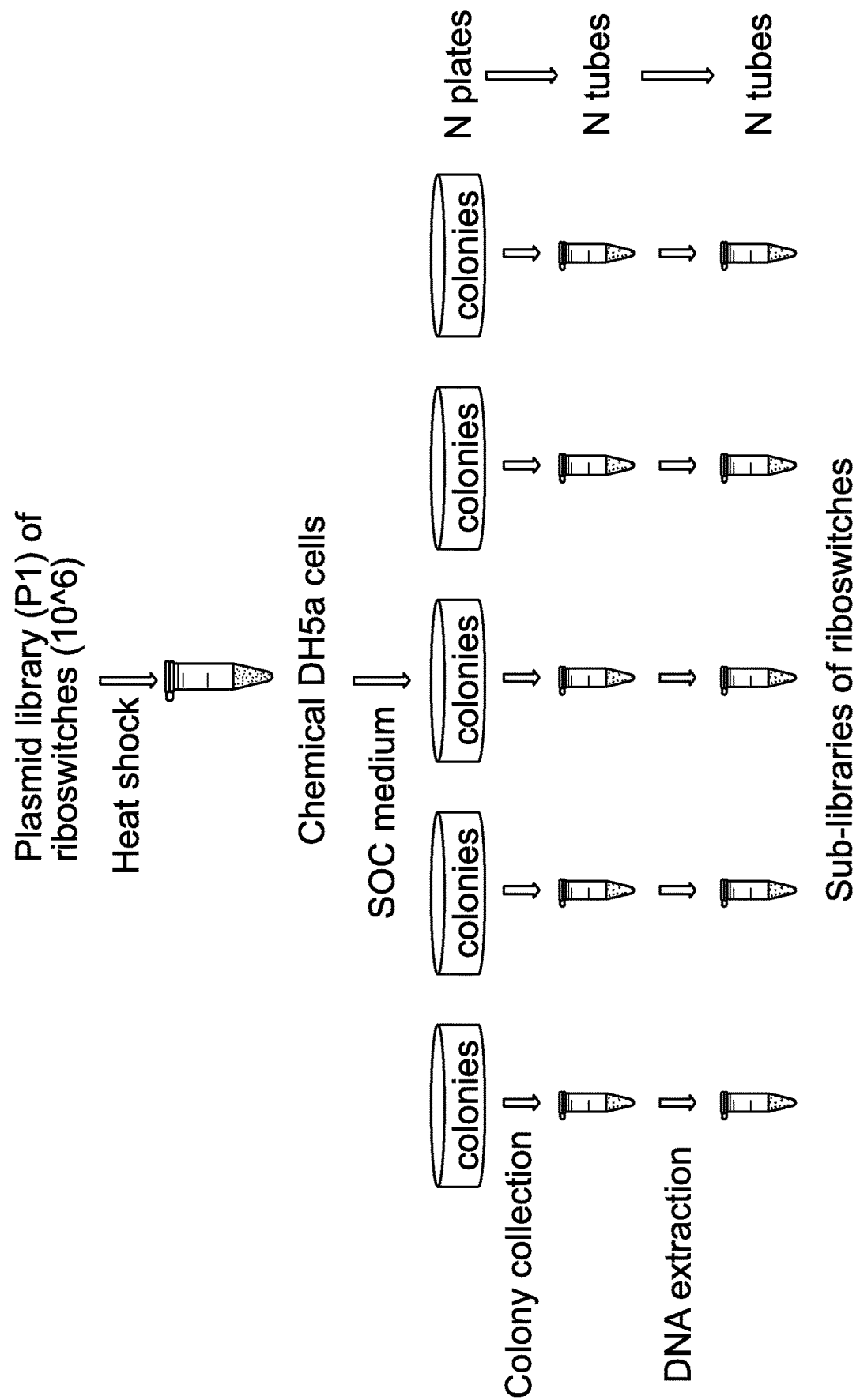
FIG. 5b. Schematic diagram of dividing plasmid library of riboswitches to sub-libraries. Plasmid library of riboswitches is transformed into chemically competent DH5a cells. Then transformed bacteria are plated into agar plates. Certain numbers of bacterial colonies are collected from each individual agar plates and plasmid DNA is extracted from individual colony collection separately. The obtained plasmid DNA from each collection of colonies forms the sub-library of riboswitch. The dividing approach can be repeated until desired size of sub-libraries is achieved.

To divide plasmid libraries into sub-libraries that are small enough to be screened using the developed cell-based assay, a strategy was utilized, as outlined in FIG. 5b, involving pooling smaller numbers of transformed bacterial colonies and extracting DNA to make plasmid sub-libraries of riboswitches. This process of dividing plasmid libraries can be performed for several rounds to obtain the required size of the sub-libraries in which a single positive event (i.e., specific aptamer/ligand binding leading to reporter gene expression) can be detected based on the sensitivity of the cell-based assay developed for screening the library, generating primary, secondary or tertiary sub-libraries, respectively. The size of sub-libraries was calculated as n (sub-library)=m (fold representation)*N (initial library size)/d (dividing fold). The "dividing fold" represents the total number of sub-libraries to obtain, and can be any number as desired. Here, we chose 100 as dividing fold for the ease of calculation. For the first round of dividing, $6×10^6$ colonies were collected, which is 6 times the number of riboswitches in the initial plasmid library to obtain greater than 99% representation ($10^6$). For the second round of dividing, 1-fold representation of the primary sub-library was chosen. For the plasmid library with $10^6$ riboswitches we built (P1), where N=$10^6$, m=6, d=100, the size of each individual sub-library is n=$6×10^4$. A total of $6×10^6$ bacterial colonies were collected into 100 individual tubes and DNA extracted from each individual tube to generate primary plasmid sub-library of riboswitches (P1S_001 through P1S_100). Using the same strategy and starting with sub-library P1S_001, as an example, the primary sub-library was further divided into 100 even smaller secondary sub-libraries named P1S_001_001 through P1S_001_100. Thus, by performing two rounds of dividing, secondary plasmid sub-libraries were generated with 600 riboswitches in each. The sub-libraries of riboswitches can be further divided by the 3rd round of dividing processes to generate tertiary plasmid sub-libraries.

The same approach was used to divide plasmid riboswitch library P2 that contains 1024 unique aptamer sequences. By collecting 100 portions of a total 5000 colonies, 100 primary sub-libraries P2S_001 to P2S_100 were generated, with each sub-library containing approximately 50 riboswitches.

Figure 5C:
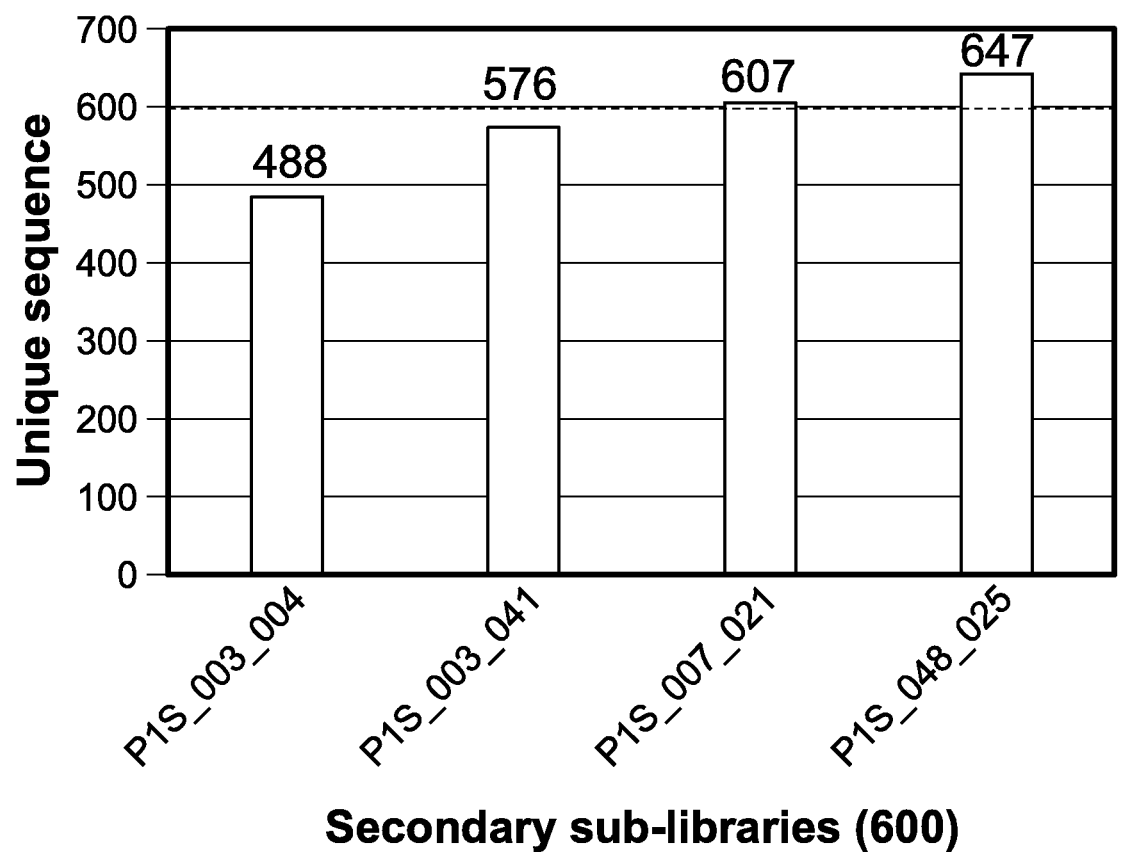
FIG. 5c. Unique sequence composition of secondary sub-libraries of the riboswitch determined by Next Generation Sequencing. Sequences with more than 12 reads from the sequencing run were considered true sequences.
Figure 5D:
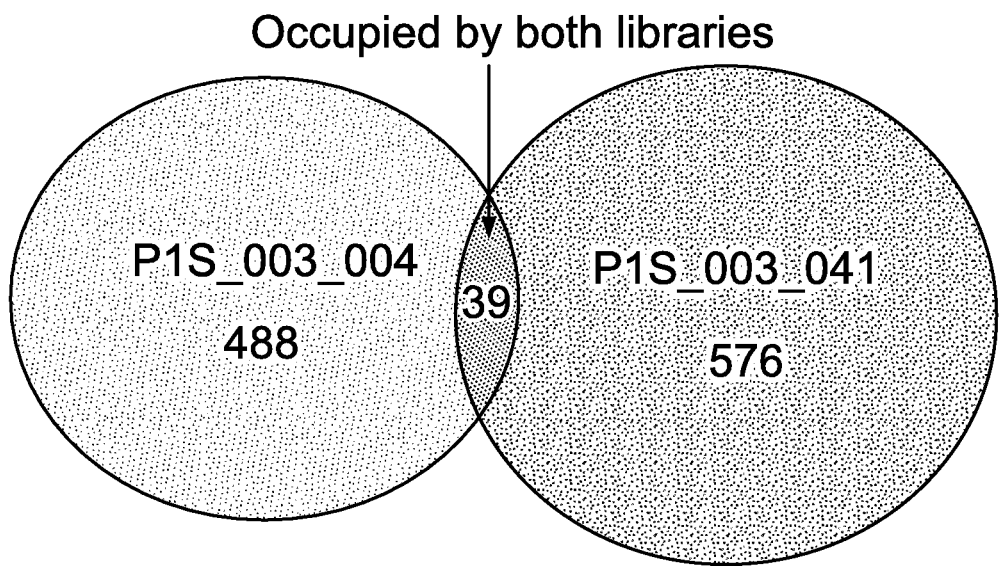
FIG. 5d. Comparison of unique sequence composition between two secondary sub-libraries that are generated from the same primary sub-library P1S_003. A pie chart indicates the number of unique sequences in each sub-library and the number of the overlapping sequences between the two libraries of riboswitches.
Figure 5E:
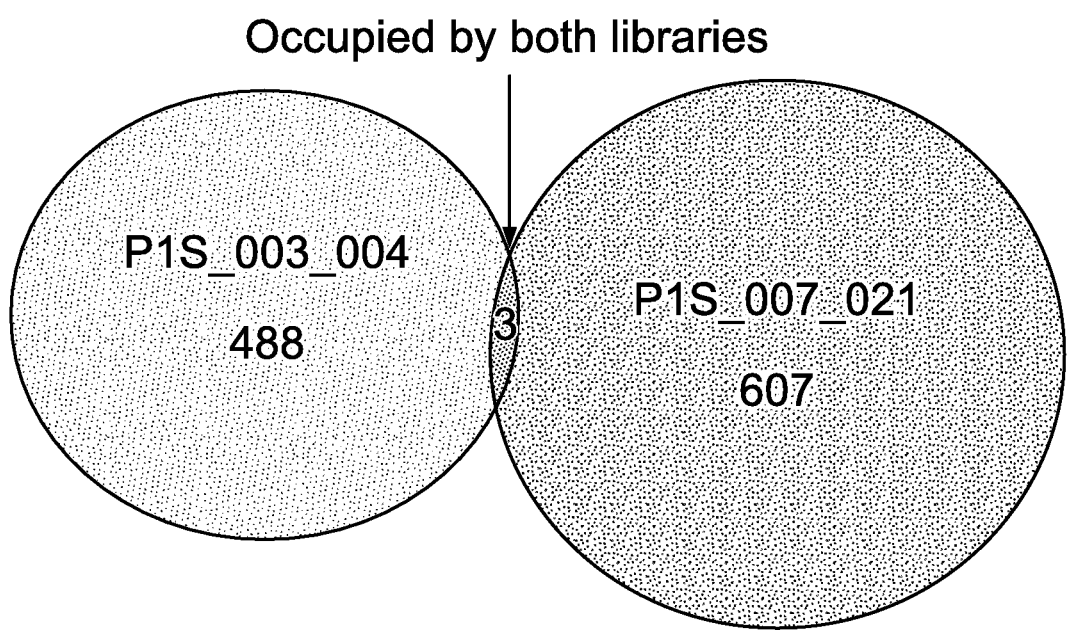
FIG. 5e. Comparison of unique sequence composition between two secondary sub-libraries that are generated from different primary sub-libraries, P1S_003 and P1S_007, respectively. A pie chart indicates the number of unique sequences in each sub-library and the number of the overlapping sequences between the two libraries of riboswitch.

To determine the composition and the quality of the above generated riboswitch libraries, next generation sequencing (NGS) was performed on the secondary plasmid sub-libraries of riboswitches that presumably contains 600 riboswitch sequences in each sub-library. Four secondary sub-libraries were selected at random where two of the secondary sub-libraries were generated from the primary sub-library P1S_003, and the other two secondary sub-libraries were generated from primary sub-libraries P1S_007 and P1S_048, respectively. As shown in FIG. 5c, each of the secondary sub-libraries contains approximately 500 or 600 unique sequences, consistent with the number of colonies that were collected for generating secondary sub-libraries. A further analysis of the NGS data indicates that between the two secondary sub-libraries (P1S_003_004 and P1S_003_041) that were generated from the same primary sub-library (P1S_003), 39 sequences are contained in both libraries (FIG. 5d). When comparing two secondary sub-libraries, P1S_003_004 and P1S_007_021, that were derived from different primary sub-libraries, P1S_003 and P1S_007, only 3 sequences are shared by both sub-libraries (FIG. 5e). These results indicate that using the above described strategy, plasmid riboswitch sub-libraries were generated with the desired number of unique sequences that are ready for mammalian cell-based screening.

Example 6

Mammalian cell-based screening for new aptamers against ligands of choice.

Figure 6A:
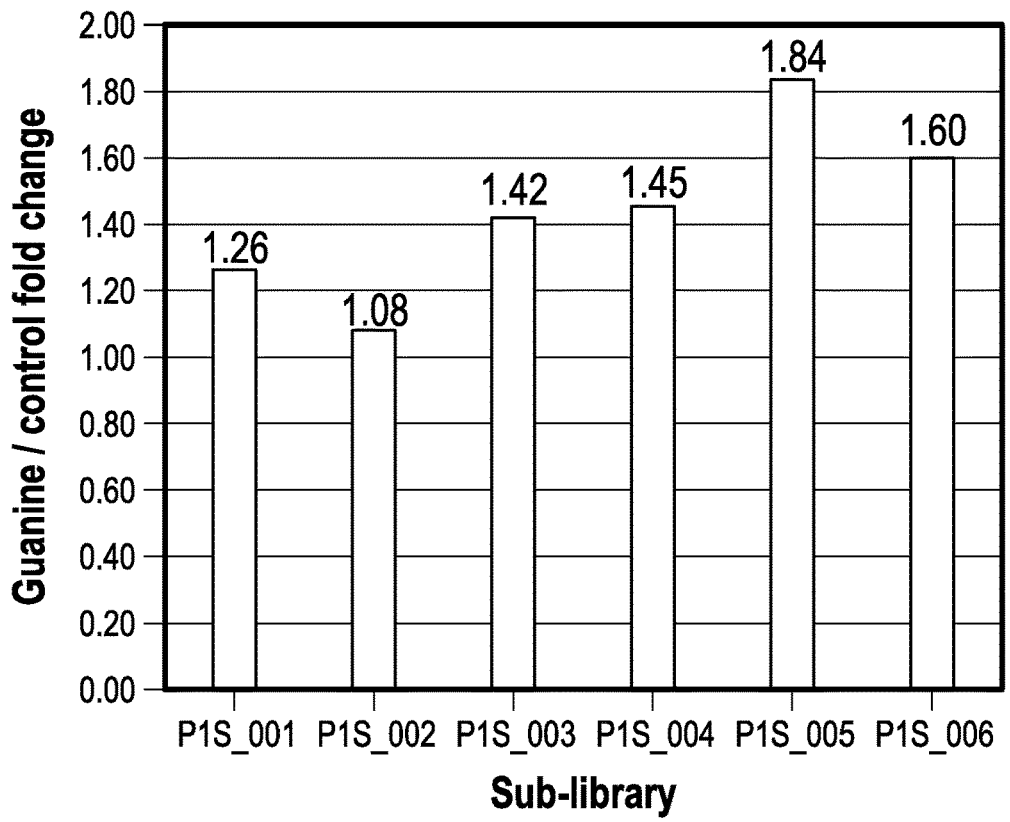
FIGS. 6a and 6b. Plasmid DNA from 6 out of 100 primary sub-libraries (60 k) (FIG. 6a) or 100 secondary sub-libraries (size of 600) (FIG. 6b) was arrayed in the format of 96-well plate, and transfected into HEK-293 cells. The fold induction of luciferase activity was calculated as luciferase activity induced with guanine divided by luciferase activity obtained without guanine treatment.
Figure 6B:
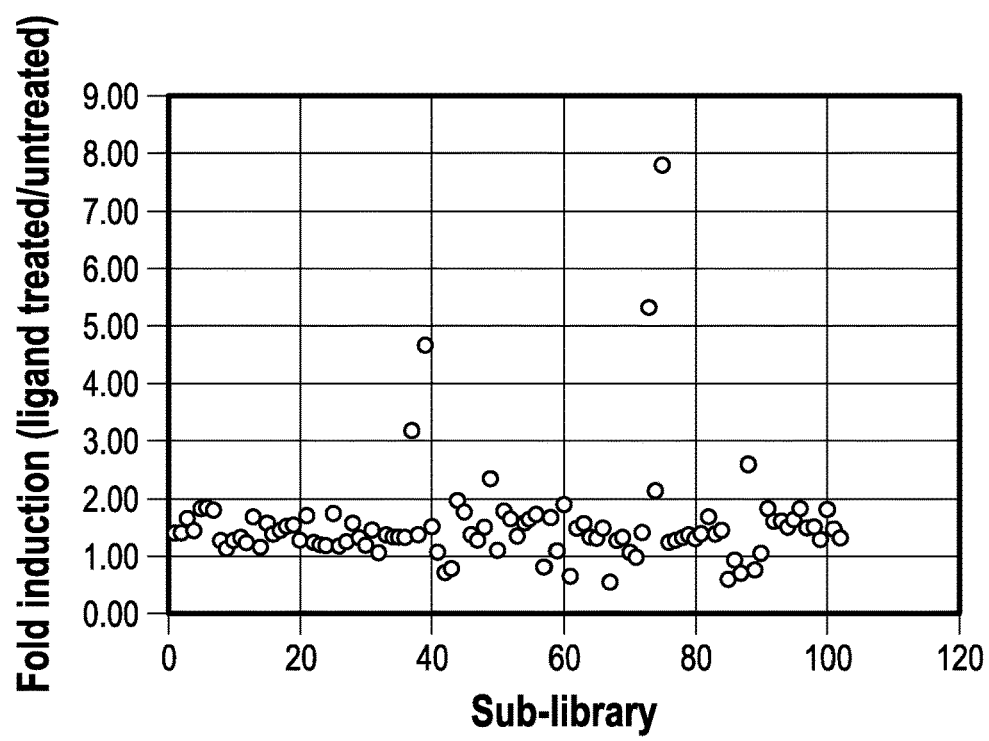

As described in Example 5, 100 primary plasmid sub-libraries (P1S_001 through P1S_100), comprising 60 k riboswitches in each pool, were constructed, and 100 secondary plasmid sub-libraries (P1S_001_001 to P1S_001_100) consisting of 600 riboswitches in each were generated by further dividing the primary sub-library P1S_001 using the same strategy. The pooled libraries can be arrayed in 96-well format to facilitate high-through screening. A preliminary screen was performed, using the luciferase reporter assay as described in Example 1, on primary sub-libraries P1S_001 to 006 as well as the sub-libraries of P1S_001, against guanine, which is against the initial aptamer sequence, as the tested ligand. The basal level of luciferase activity generated by constructs from either primary sub-libraries or secondary sub-libraries varied significantly from that of xpt-G17 construct (data not shown), suggesting that changes in the aptamer sequence by randomizing bases at the selected positions impacted the inclusion/exclusion of the stop codon-containing exon to various extent, therefore affecting the basal luciferase expression. Following guanine treatment, although cells transfected with the 60 k primary sub-library P1S_005 generated 1.8-fold induction of luciferase activity in comparison to untreated cells (FIG. 6a), more than 2-fold induction of luciferase was not discovered when using guanine as the ligand. However, 7 of the 100 secondary sub-libraries yielded more than 2-fold induction of luciferase activity upon guanine treatment, with sub-library P1S_001_075 generating 7.8-fold induction (FIG. 6b). In the sensitivity assay described in Example 4, 6.3-fold induction was detected when there was 1 xpt-G17 riboswitch among 500 non-ligand responding molecules. Based on this sensitivity test, the result (7.8 fold) from this preliminary screening of the sub-library P1S_001_075 suggests that there is either 1 riboswitch out of 600 that is functionally equivalent to xpt-G17, or there are several weaker riboswitches of which the sum of induced luciferase activity is comparable to that of xpt-G17.

Figure 6C:
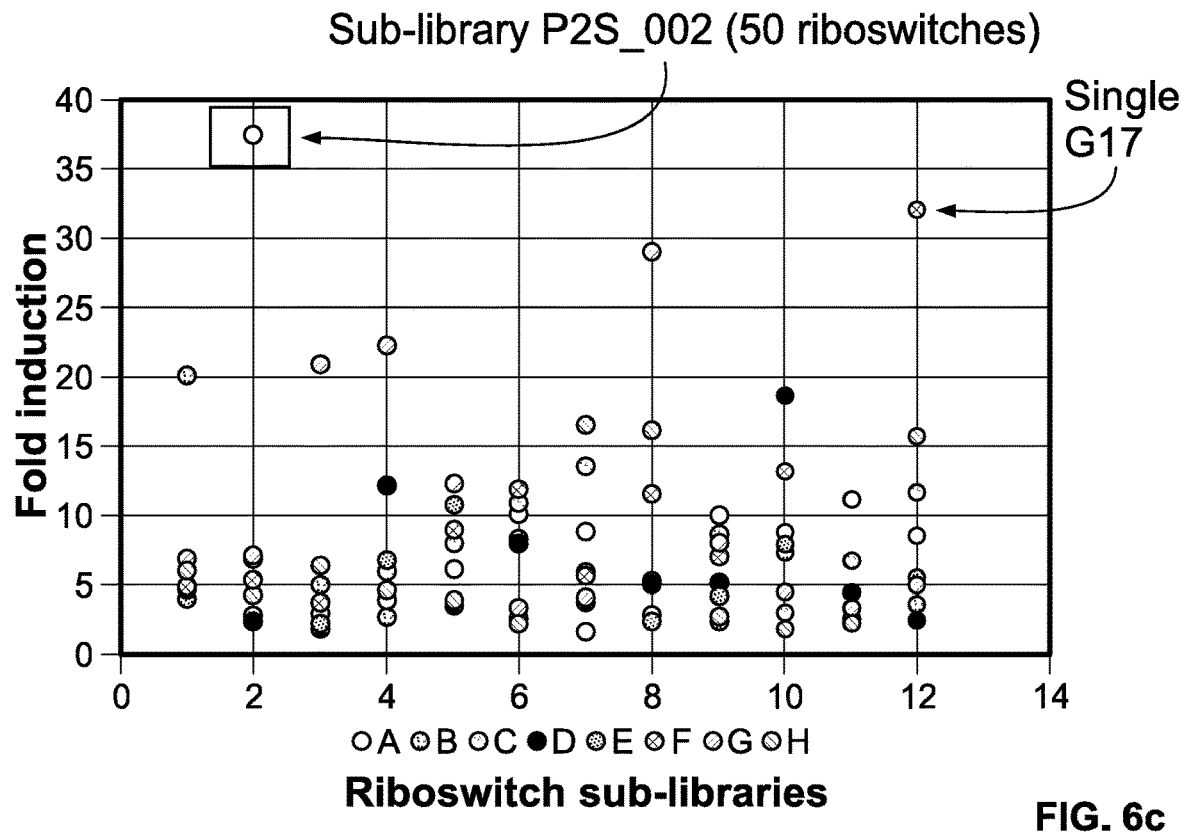
FIG. 6c. Riboswitch sub-library screening results using nicotinamide adenine dinucleotide (NAD+) as ligand. The sub-libraries of P2 riboswitch library were arrayed in 96-well format. HEK 293 cells were plated in 96-well plate and transfected with riboswitch library DNAs. Four hours after transfection, cells were treated with 100 µM NAD+. Luciferase activity was measured 20 hours after NAD+ treatment. The fold induction was calculated as the ratio of the luciferase activity obtained from NAD+ treated cells divided by luciferase activity obtained from cells without NAD+ treatment. Each dot in the dot plot represents the fold induction from a sub-library or G17 construct as indicated.

To further demonstrate the applicability of the mammalian cell-based screening of the present invention for functional aptamers-containing riboswitches and to discover new aptamers with improved activity in responding to a desired ligand, the sub-libraries of plasmid riboswitch library P2 were screened in a 96-well format with NAD+. The nucleotide bases at the randomized positions in the xpt-guanine aptamer have been linked to riboswitch activity tuning and named tune box (Stoddard, et al. J Mol Biol. 2013 May 27; 425(10):1596-611). Therefore, changes of nucleotides at these positions potentially generate sequences that have altered riboswitch activity in response to the ligand treatment. Due to the nature of guanine and its low applicability in vivo, NAD+ was chosen as ligand for potential new aptamers. This choice of ligand was based upon the above results from screening the Prestwick compound library against the parental xpt-G17 riboswitch, and discovering that NAD+ can regulate the guanine riboswitch, generating approximately 40-fold induction at 100 µM concentration. In an attempt to generate aptamer sequences that have improved riboswitch activity against NAD+, we generated and screened the sub-libraries of P2 (having changes of nucleotides at the above-mentioned 5 positions in the aptamer) using luciferase as reporter gene. As shown in FIG. 6c, multiple sub-libraries, approximately 50 riboswitches in each, yielded more than 10 fold induction of luciferase expression in response to the treatment of 100 µM NAD+, with one of the sub-libraries, P2S_002, generating 37 fold induction, whereas a single xpt-G17 riboswitch construct showed 32 fold induction in response to the treatment of NAD+ at same concentration.

Figure 6D:
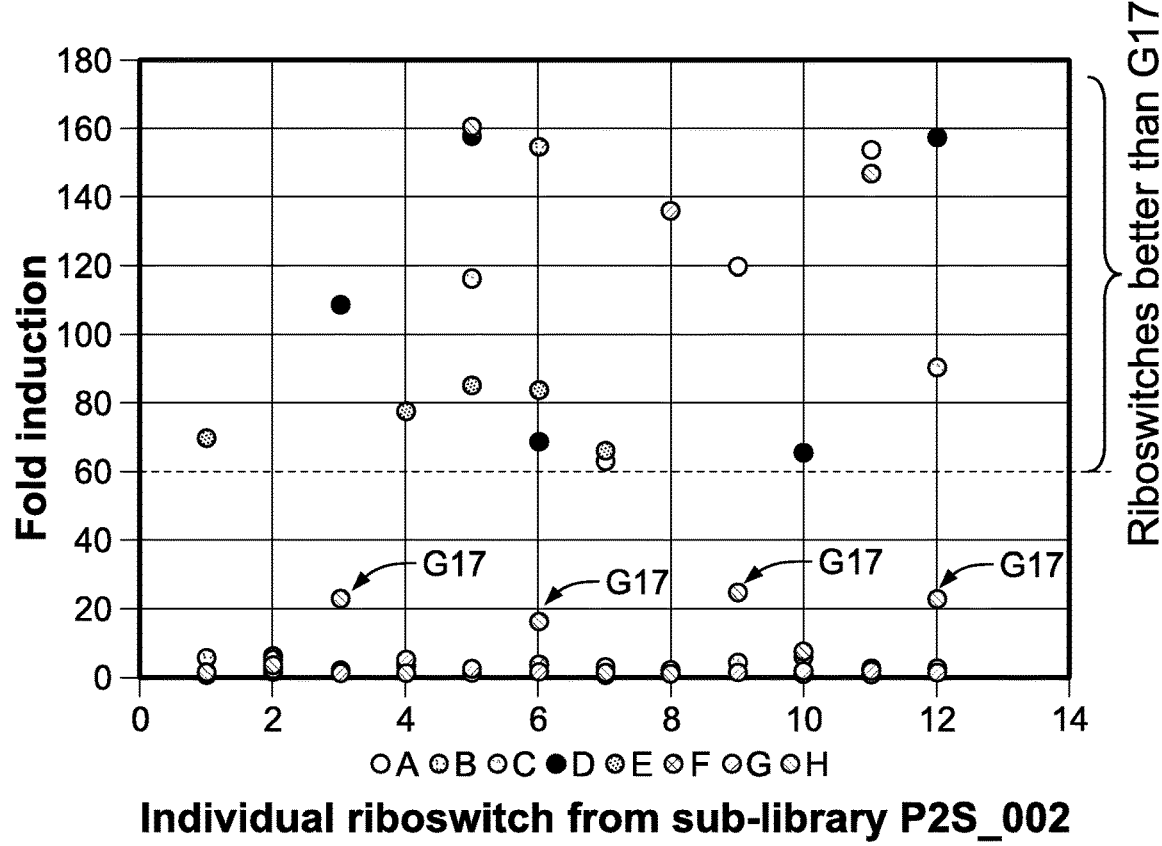
FIG. 6d. Riboswitch screening results using NAD+ as ligand. Each individual riboswitch construct was arrayed in 96-well format. HEK 293 cells were plated in 96-well plate and transfected with riboswitch constructs. 4 hours after transfection, cells were treated with 100 µM NAD+. Luciferase activity was measured 20 hours after NAD+ treatment. The fold induction was calculated as the ratio of the luciferase activity obtained from NAD+ treated cells divided by luciferase activity obtained from cells without NAD+ treatment. Each dot in the dot plot represents the fold induction from each single riboswitch construct or G17 construct as indicated.

These screening results indicate that among the approximately 50 riboswitches in the sub-libraries that yielded more than 10 fold induction of luciferase expression, there are riboswitches that can produce minimally 10 fold induction, assuming all the riboswitches in the library respond to NAD+ treatment. In the sub-library P2S_002 that yielded 37 fold induction, which is higher than the fold induction generated by G17, there is at least 1 riboswitch that functions much better than G17. To further prove this, 96 single constructs derived from sub-library P2S_002 were screened. As shown in FIG. 6d, though multiple constructs lost or produced less induction than G17, a number of single constructs produced higher fold induction than the G17 construct, indicating that nucleotide changes in the tune box dramatically affect the riboswitch activity in responding to ligand treatment in cells. Using this approach, we identified a number of different tune box sequences (as shown in Table 2), with which the riboswitches produced higher fold induction of luciferase than the G17 construct upon NAD+ treatment, with multiple aptamer sequences producing more than 100 fold induction.

TABLE 2

Riboswitches with improved reporter gene expression in mammalian cells in response to ligand, NAD+.
Tune box sequences are underlined.

| SEQ ID NO: | Construct | Sequence |
|---|---|---|
| 13 | G17 | ATA<u>AT</u>CGCGTGGATATGGCACGC<u>AA</u>GTTTCTACCGGGCACCGTAAATGTCCGACT |
| 14 | #02 | ATA<u>AC</u>CGCGTGGATATGGCACGC<u>GG</u>GTTTCTACCGGGCACCGTAAATGTCCGACT |
| 15 | #16 | ATA<u>GC</u>CGCGTGGATATGGCACGC<u>GG</u>GTTTCTACCGGGCACCGTAAATGTCCGACT |
| 16 | #17 | ATA<u>AGG</u>GCGTGGATATGGCACGC<u>TC</u>GTTTCTACCGGGCACCGTAAATGTCCGACT |
| 17 | #21 | ATA<u>AAT</u>GCGTGGATATGGCACGC<u>AT</u>GTTTCTACCGGGCACCGTAAATGTCCGACT |
| 18 | #26 | ATA<u>AGC</u>GCGTGGATATGGCACGC<u>GC</u>GTTTCTACCGGGCACCGTAAATGTCCGACT |

TABLE 2-continued

Riboswitches with improved reporter gene expression in mammalian cells in response to ligand, NAD+.
Tune box sequences are underlined.

| SEQ ID NO: | Construct | Sequence |
|---|---|---|
| 19 | #29 | ATA<u>GT</u>GCGTGGATATGGCACGC<u>C</u>AGTTTCTACCGGGCACCGTAAATGTCCGACT |
| 20 | #31 | ATA<u>AA</u>GGCGTGGATATGGCACGC<u>C</u>GGTTTCTACCGGGCACCGTAAATGTCCGACT |
| 21 | #33 | ATA<u>GT</u>TGCGTGGATATGGCACGC<u>AA</u>GTTTCTACCGGGCACCGTAAATGTCCGACT |
| 22 | #36 | ATA<u>GC</u>GGCGTGGATATGGCACGC<u>T</u>GGTTTCTACCGGGCACCGTAAATGTCCGACT |
| 23 | #41 | ATA<u>AT</u>GGCGTGGATATGGCACGC<u>T</u>AGTTTCTACCGGGCACCGTAAATGTCCGACT |
| 24 | #46 | ATA<u>AT</u>TGCGTGGATATGGCACGC<u>AA</u>GTTTCTACCGGGCACCGTAAATGTCCGACT |
| 25 | #54 | ATA<u>AT</u>TGCGTGGATATGGCACGC<u>G</u>AGTTTCTACCGGGCACCGTAAATGTCCGACT |
| 26 | #61 | ATA<u>AT</u>CGCGTGGATATGGCACGC<u>G</u>AGTTTCTACCGGGCACCGTAAATGTCCGACT |
| 27 | #69 | ATA<u>AC</u>TGCGTGGATATGGCACGC<u>GG</u>GTTTCTACCGGGCACCGTAAATGTCCGACT |

Figure 6E:
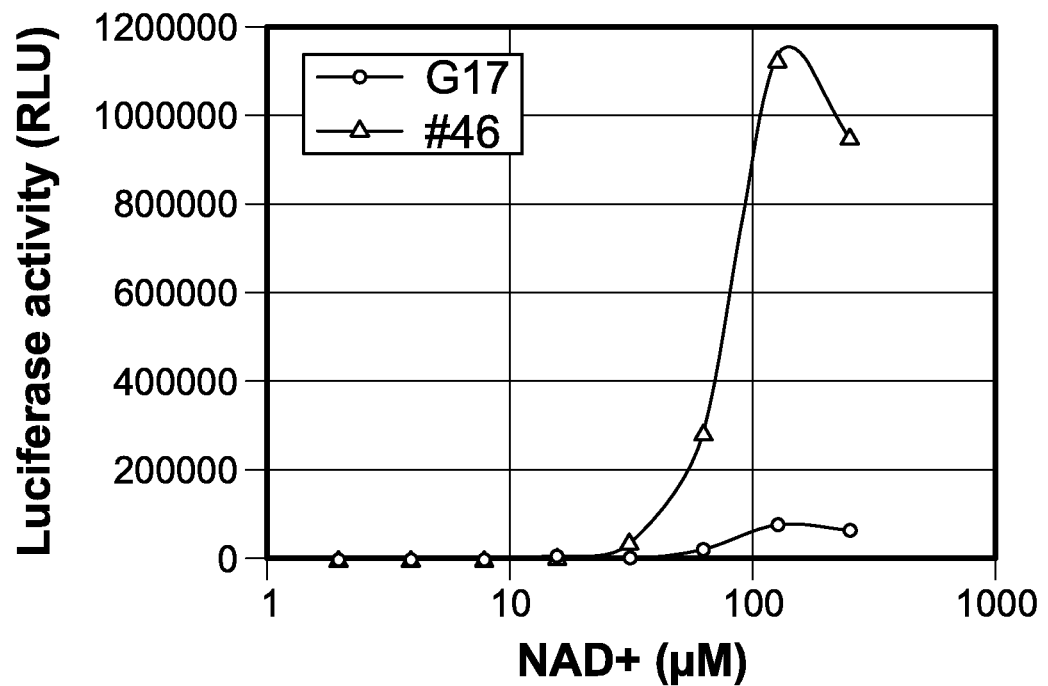
FIGS. 6e and 6f. Construct with new aptamer sequence show enhanced response to NAD+ treatment in a dose dependent manner compared to the G17 riboswitch. HEK 293 cells were transfected with the G17 or construct #46 with new aptamer sequence. 4 hours after transfection, cells were treated with different doses of NAD+. Luciferase activity was measured 20 hours after NAD+ treatment. The fold induction was calculated as the ratio of the luciferase activity obtained from NAD+ treated cells divided by luciferase activity obtained from cells without NAD+ treatment.
Figure 6F:
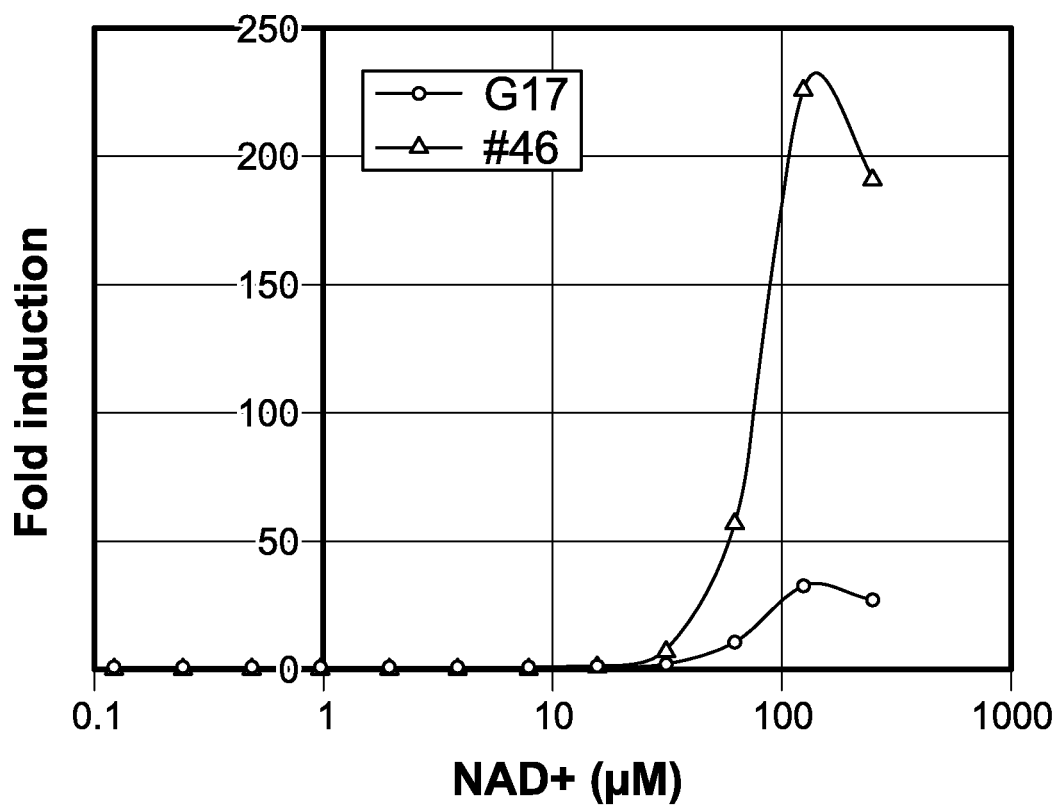

One of the new constructs, #46, was further tested. As shown in FIG. 6e and FIG. 6f, new construct #46 responded to NAD+ treatment in a dose-dependent manner and showed superior improvement in the level of induced reporter gene expression as well as in the induction fold when compared with G17 construct. The new constructs also have improved gene regulation in response to guanine treatment (data not shown).

Thus, the present invention provides an approach where a relatively large riboswitch library can be divided into smaller riboswitch sub-library that is screenable through a mammalian cell-based assay. Moreover, from the riboswitch library, new sequences that have improved riboswitch activities in mammalian cells were discovered.

REFERENCES

1. Mandal, Maumita, Benjamin Boese, Jeffrey E. Barrick, Wade C. Winkler, and Ronald R. Breaker. "Riboswitches Control Fundamental Biochemical Pathways in *Bacillus Subtilis* and Other Bacteria." Cell 113, no. 5 (May 30, 2003): 577-86.
2. Mandal, Maumita, and Ronald R. Breaker. "Adenine Riboswitches and Gene Activation by Disruption of a Transcription Terminator." Nature Structural & Molecular Biology 11, no. 1 (January 2004): 29-35. doi:10.1038/nsmb710.
3. Mulhbacher, Jerome, and Daniel A. Lafontaine. "Ligand Recognition Determinants of Guanine Riboswitches." Nucleic Acids Research 35, no. 16 (2007): 5568-80. doi:10.1093/nar/gkm572.
4. Serganov, Alexander, Yu-Ren Yuan, Olga Pikovskaya, Anna Polonskaia, Lucy Malinina, Anh Tuan Phan, Claudia Hobartner, Ronald Micura, Ronald R. Breaker, and Dinshaw J. Patel. "Structural Basis for Discriminative Regulation of Gene Expression by Adenine- and Guanine-Sensing mRNAs." Chemistry & Biology 11, no. 12 (December 2004): 1729-41. doi:10.1016/j.chembiol.2004.11.018.
5. Edwards, Andrea L., and Robert T. Batey. "A Structural Basis for the Recognition of 2'-deoxyguanosine by the Purine Riboswitch." Journal of Molecular Biology 385, no. 3 (Jan. 23, 2009): 938-48. doi:10.1016/j.jmb.2008.10.074.
6. Batey, Robert T., Sunny D. Gilbert, and Rebecca K. Montange. "Structure of a Natural Guanine-Responsive Riboswitch Complexed with the Metabolite Hypoxanthine." Nature 432, no. 7015 (Nov. 18, 2004): 411-15. doi:10.1038/nature03037.
7. Serganov, Alexander, Yu-Ren Yuan, Olga Pikovskaya, Anna Polonskaia, Lucy Malinina, Anh Tuan Phan, Claudia Hobartner, Ronald Micura, Ronald R. Breaker, and Dinshaw J. Patel. "Structural Basis for Discriminative Regulation of Gene Expression by Adenine- and Guanine-Sensing mRNAs." Chemistry & Biology 11, no. 12 (December 2004): 1729-41. doi:10.1016/j.chembiol.2004.11.018.
8. Ellington, A. D., and J. W. Szostak. "In Vitro Selection of RNA Molecules That Bind Specific Ligands." Nature 346, no. 6287 (Aug. 30, 1990): 818-22. doi:10.1038/346818a0.
9. Tuerk, C., and L. Gold. "Systematic Evolution of Ligands by Exponential Enrichment: RNA Ligands to Bacteriophage T4 DNA Polymerase." Science (New York, N.Y.) 249, no. 4968 (Aug. 3, 1990): 505-10.
10. Ozer, Abdullah, John M. Pagano, and John T. Lis. "New Technologies Provide Quantum Changes in the Scale, Speed, and Success of SELEX Methods and Aptamer Characterization." Molecular Therapy. Nucleic Acids 3 (2014): e183. doi:10.1038/mtna.2014.34.
11. Kebschull, Justus M., and Anthony M. Zador. "Sources of PCR-Induced Distortions in High-Throughput Sequencing Data Sets." Nucleic Acids Research 43, no. 21 (Dec. 2, 2015): e143. doi:10.1093/nar/gkv717.

We claim:

1. A method for selecting an aptamer that binds a ligand in eukaryotic cells comprising the steps of:
   a. providing a library of aptamers,
   b. introducing the members of the library of aptamers into a polynucleotide cassette for the ligand-mediated expression of a reporter gene to create a library of riboswitches,
   c. introducing the polynucleotide cassette comprising the library of riboswitches into eukaryotic cells in vitro, and
   d. contacting the eukaryotic cells with a ligand, and
   e. measuring expression of the reporter gene,
   wherein the polynucleotide cassette comprises an alternatively-spliced exon, flanked by a 5' intron and a 3' intron, and a riboswitch comprising (i) an effector region comprising a stem that includes the 5' splice site sequence of the 3' intron, and (ii) an aptamer, wherein the alternatively-spliced exon comprises a stop codon that is in-frame with the reporter gene when the alternatively-spliced exon is spliced into the reporter gene mRNA.

2. The method of claim 1, wherein the library of aptamers comprises aptamers having one or more randomized nucleotides.

3. The method of claim 1, wherein the ligand is a small molecule.

4. The method of claim 3, wherein the ligand is a molecule produced by the eukaryotic cell selected from the group consisting of a metabolite, nucleic acid, vitamin, co-factor, lipid, monosaccharide, and second messenger.

5. The method of claim 1, wherein the eukaryotic is selected from a mammalian cell, an insect cell, a plant cell, and a yeast cell.

6. The method of claim 1, wherein the reporter gene is selected from the group consisting of a fluorescent protein, luciferase, β-galactosidase and horseradish peroxidase.

7. The method of claim 1, wherein the expression of the reporter gene is greater than about 10-fold higher when the ligand specifically binds the aptamer than the reporter gene expression levels when the ligand is absent.

8. The method of claim 1, wherein, the 5' and 3' introns are derived from intron 2 of the human β-globin gene.

9. The method of claim 1, wherein the 5' and 3' introns are each independently from about 50 to about 300 nucleotides in length.

10. The method of claim 1, wherein the 5' and 3' introns are each independently from about 125 to about 240 nucleotides in length.

11. The method of claim 1, wherein the effector region stem is about 7 to about 20 base pairs in length.

12. The method of claim 1, wherein the effector region stem is 8 to 11 base pairs in length.

13. The method of claim 1, wherein the alternatively-spliced exon is derived from the group consisting of exon 2 of the human dihydrofolate reductase gene, mutant human Wilms tumor 1 exon 5, mouse calcium/calmodulin-dependent protein kinase II delta exon 16, and SIRT1 exon 6.

14. The method of claim 1, wherein the alternatively-spliced exon is the modified exon 2 from human DHFR.

15. The method of claim 1, wherein, wherein the alternatively-spliced exon is synthetic.

16. The method of claim 1, wherein the alternatively-spliced exon has been modified by one or more of the group consisting of altering the sequence of an exon splice enhancer, altering the sequence of exon splice silencer, adding an exon splice enhancer, and adding an exon splice silencer.

17. The method of claim 1, wherein the library of aptamers is divided into a smaller aptamer library before introducing into the polynucleotide cassettes comprising the steps:
  a. providing a randomized aptamer library wherein the aptamers in the library comprise 5' and 3' constant regions and one or more randomized nucleotides,
  b. performing a two-cycle PCR using the randomized aptamer library as the template and a first primer and second primer that are complementary to the 5' and 3' constant regions, the primers each including one of a plurality of tag sequences,
  c. isolating the products of the two-cycle PCR, and
  d. PCR amplifying a subset of the isolated products of the two-cycle PCR using primers complementary to a subset of the 5' and 3' tag sequences.

18. The method of claim 17, wherein the first or second primer in the two-cycle PCR comprises a label selected from the group consisting of biotin, digoxigenin (DIG), bromodeoxyuridine (BrdU), fluorophore, and a chemical group used in click chemistry.

19. The method according to claim 1, wherein the library of riboswitches is divided into one or more sub-libraries of riboswitches before being introduced into the eukaryotic cells.

20. The method of claim 19, wherein the library of riboswitches is subdivided into sub-libraries comprising the steps of:
  a. introducing the riboswitch library into bacteria;
  b. collecting bacterial clones and extracting plasmid DNA to obtain plasmid sub-libraries of riboswitches to generate one or more primary sub-libraries;
  c. optionally, generating secondary sub-libraries of riboswitches from a primary plasmid sub-library of riboswitches by introducing a primary sub-library into bacteria, collecting bacterial clones and isolating the plasmid DNA.

21. A method for selecting a ligand that binds an aptamer in a eukaryotic cell comprising the steps of:
  a. providing a library of ligands,
  b. providing a polynucleotide cassette for the ligand-mediated expression of a reporter gene,
  c. introducing the polynucleotide cassette into the eukaryotic cell in vitro,
  d. contacting individual groups of the eukaryotic cell with members of the library of ligands, and
  e. measuring the expression of the reporter gene, wherein the polynucleotide cassette comprises an alternatively-spliced exon, flanked by a 5' intron and a 3' intron, and a riboswitch comprising (i) an effector region comprising a stem that includes the 5' splice site sequence of the 3' intron, and (ii) an aptamer, wherein the alternatively-spliced exon comprises a stop codon that is in-frame with the reporter gene when the alternatively-spliced exon is spliced into the reporter gene mRNA.

22. The method of claim 21, wherein the ligand is a small molecule.

23. The method of claim 21, wherein the ligand is a molecule produced by the eukaryotic cell.

24. The method of claim 23, wherein the ligand is a metabolite, nucleic acid, vitamin, co-factor, lipid, monosaccharide, and second messenger.

25. The method of claim 21, wherein the eukaryotic cell is selected from the group consisting of a mammalian cell, an insect cell, a plant cell, and a yeast cell.

26. The method of claim 21, wherein the reporter gene is selected from the group consisting of a fluorescent protein, luciferase, β-galactosidase and horseradish peroxidase.

27. The method of claim 21, wherein the reporter gene is selected from the group consisting of a cytokine, a signaling molecule, a growth hormone, an antibody, a regulatory RNA, a therapeutic protein, or a peptide.

28. The method of claim 21, wherein the expression of the reporter gene is greater than about 10-fold higher when the ligand specifically binds the aptamer than the reporter gene expression levels when the ligand is absent.

29. The method of claim 21, wherein, the 5' and 3' introns are derived from intron 2 of the human β-globin gene.

30. The method of claim 21, wherein the 5' and 3' introns are each independently from about 50 to about 300 nucleotides in length.

31. The method of claim 21, wherein the 5' and 3' introns are each independently from about 125 to about 240 nucleotides in length.

32. The method of claim 21, wherein the effector region stem is about 7 to about 20 base pairs in length.

33. The method of claim 21, wherein the effector region stem is 8 to 11 base pairs in length.

34. The method of claim 21, wherein the alternatively-spliced exon is derived from the group consisting of exon 2 of the human dihydrofolate reductase gene, mutant human Wilms tumor 1 exon 5, mouse calcium/calmodulin-dependent protein kinase II delta exon 16, and SIRT1 exon 6.

35. The method of claim 21, wherein the alternatively-spliced exon is the modified exon 2 from human DHFR.

36. The method of claim 21, wherein, wherein the alternatively-spliced exon is synthetic.

37. The method of claim 21, wherein the alternatively-spliced exon has been modified by one or more of the group consisting of altering the sequence of an exon splice enhancer, altering the sequence of exon splice silencer, adding an exon splice enhancer, and adding an exon splice silencer.

38. An aptamer encoded by a sequence comprising the sequence of SEQ ID NO: 14 to 27.

39. An aptamer encoded by a sequence comprising the sequence SEQ ID NO: 24.

* * * * *

SEQUENCE LISTING

```
<160> NUMBER OF SEQ ID NOS: 27

<210> SEQ ID NO 1
<211> LENGTH: 69
<212> TYPE: DNA
<213> ORGANISM: Artificial Sequence
<220> FEATURE:
<223> OTHER INFORMATION: xpt-A8

<400> SEQUENCE: 1
```

```
gtaatgtata atcgcgtgga tatggcacgc aagtttctac cgggcaccgt aaatgtccga    60
ttacattac                                                            69

<210> SEQ ID NO 2
<211> LENGTH: 73
<212> TYPE: DNA
<213> ORGANISM: Artificial Sequence
<220> FEATURE:
<223> OTHER INFORMATION: add-G6

<400> SEQUENCE: 2
gtaatgtgta taatcctaat gatatggttt gggagtttct accaagagcc ttaaactctt    60
gactacacat tac                                                       73

<210> SEQ ID NO 3
<211> LENGTH: 73
<212> TYPE: DNA
<213> ORGANISM: Artificial Sequence
<220> FEATURE:
<223> OTHER INFORMATION: add-A6

<400> SEQUENCE: 3
gtaatgtgta taatcctaat gatatggttt gggagtttct accaagagcc ttaaactctt    60
gattacacat tac                                                       73

<210> SEQ ID NO 4
<211> LENGTH: 66
<212> TYPE: DNA
<213> ORGANISM: Artificial Sequence
<220> FEATURE:
<223> OTHER INFORMATION: gdg6-A8

<400> SEQUENCE: 4
gtaatgtaca gggtagcata atgggctact gaccccgccg ggaaacctat ttcccgatta    60
cattac                                                               66

<210> SEQ ID NO 5
<211> LENGTH: 66
<212> TYPE: DNA
<213> ORGANISM: Artificial Sequence
<220> FEATURE:
<223> OTHER INFORMATION: gdg6-G8

<400> SEQUENCE: 5
gtaatgtaca gggtagcata atgggctact gaccccgccg ggaaacctat ttcccgacta    60
cattac                                                               66

<210> SEQ ID NO 6
<211> LENGTH: 69
<212> TYPE: DNA
<213> ORGANISM: Artificial Sequence
<220> FEATURE:
<223> OTHER INFORMATION: Ydhl-G8

<400> SEQUENCE: 6
gtaatgtata acctcaataa tatggtttga gggtgtctac caggaaccgt aaaatcctga    60
ctacattac                                                            69

<210> SEQ ID NO 7
<211> LENGTH: 73
<212> TYPE: DNA
<213> ORGANISM: Artificial Sequence
```

```
<220> FEATURE:
<223> OTHER INFORMATION: Ydh1-A6

<400> SEQUENCE: 7
gtaatgtgta taacctcaat aatatggttt gagggtgtct accaggaacc gtaaaatcct    60
gattacacat tac                                                      73

<210> SEQ ID NO 8
<211> LENGTH: 75
<212> TYPE: DNA
<213> ORGANISM: Artificial Sequence
<220> FEATURE:
<223> OTHER INFORMATION: yxj-A6

<400> SEQUENCE: 8
gtaatgtgta tatgatcagt aatatggtct gattgtttct acctagtaac cgtaaaaaac    60
tagattacac attac                                                    75

<210> SEQ ID NO 9
<211> LENGTH: 153
<212> TYPE: DNA
<213> ORGANISM: Artificial Sequence
<220> FEATURE:
<223> OTHER INFORMATION: Aptamer library generation sequence
<220> FEATURE:
<221> NAME/KEY: misc_feature
<222> LOCATION: (57)..(59)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(83)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t

<400> SEQUENCE: 9
gacttcggtc tcatccagag aatgaaaaaa aaatcttcag tagaaggtaa tgtatannng    60
cgtggatatg gcacgcnngn nnncnccggg caccgtaaat gtccgactac attacgcacc   120
attctaaaga ataacagtga agagaccaga cgg                                153

<210> SEQ ID NO 10
<211> LENGTH: 153
<212> TYPE: DNA
<213> ORGANISM: Artificial Sequence
<220> FEATURE:
<223> OTHER INFORMATION: Plasmid riboswitch library (P2)
<220> FEATURE:
<221> NAME/KEY: misc_feature
<222> LOCATION: (57)..(59)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t

<400> SEQUENCE: 10
gacttcggtc tcatccagag aatgaaaaaa aaatcttcag tagaaggtaa tgtatannng    60
cgtggatatg gcacgcnngt ttctaccggg caccgtaaat gtccgactac attacgcacc   120
attctaaaga ataacagtga agagaccaga cgg                                153
```

<210> SEQ ID NO 11
<211> LENGTH: 52
<212> TYPE: DNA
<213> ORGANISM: Artificial Sequence
<220> FEATURE:
<223> OTHER INFORMATION: DHFR_F

<400> SEQUENCE: 11
gacttcggtc tcatccagag aatgaaaaaa aaatcttcag tagaaggtaa tg    52

<210> SEQ ID NO 12
<211> LENGTH: 39
<212> TYPE: DNA
<213> ORGANISM: Artificial Sequence
<220> FEATURE:
<223> OTHER INFORMATION: IVS_R

<400> SEQUENCE: 12
ccgtctggtc tcttcactgt tattctttag aatggtgcg    39

<210> SEQ ID NO 13
<211> LENGTH: 32
<212> TYPE: DNA
<213> ORGANISM: Artificial Sequence
<220> FEATURE:
<223> OTHER INFORMATION: G17

<400> SEQUENCE: 13
gtataatcgc gtggatatgg cacgcaagtt tc    32

<210> SEQ ID NO 14
<211> LENGTH: 32
<212> TYPE: DNA
<213> ORGANISM: Artificial Sequence
<220> FEATURE:
<223> OTHER INFORMATION: #02 tune box

<400> SEQUENCE: 14
gtataaccgc gtggatatgg cacgcgggtt tc    32

<210> SEQ ID NO 15
<211> LENGTH: 32
<212> TYPE: DNA
<213> ORGANISM: Artificial Sequence
<220> FEATURE:
<223> OTHER INFORMATION: #16 tune box

<400> SEQUENCE: 15
gtatagccgc gtggatatgg cacgcgggtt tc    32

<210> SEQ ID NO 16
<211> LENGTH: 32
<212> TYPE: DNA
<213> ORGANISM: Artificial Sequence
<220> FEATURE:
<223> OTHER INFORMATION: #17 tune box

<400> SEQUENCE: 16
gtataagggc gtggatatgg cacgctcgtt tc    32

<210> SEQ ID NO 17
<211> LENGTH: 32
<212> TYPE: DNA
<213> ORGANISM: Artificial Sequence
<220> FEATURE:
<223> OTHER INFORMATION: #21 tune box

<400> SEQUENCE: 17
gtataaatgc gtggatatgg cacgcatgtt tc                                32

<210> SEQ ID NO 18
<211> LENGTH: 32
<212> TYPE: DNA
<213> ORGANISM: Artificial Sequence
<220> FEATURE:
<223> OTHER INFORMATION: #26 tune box

<400> SEQUENCE: 18
gtataagcgc gtggatatgg cacgcgcgtt tc                                32

<210> SEQ ID NO 19
<211> LENGTH: 32
<212> TYPE: DNA
<213> ORGANISM: Artificial Sequence
<220> FEATURE:
<223> OTHER INFORMATION: #29 tune box

<400> SEQUENCE: 19
gtatagtggc gtggatatgg cacgccagtt tc                                32

<210> SEQ ID NO 20
<211> LENGTH: 32
<212> TYPE: DNA
<213> ORGANISM: Artificial Sequence
<220> FEATURE:
<223> OTHER INFORMATION: #31 tune box

<400> SEQUENCE: 20
gtataaaggc gtggatatgg cacgccggtt tc                                32

<210> SEQ ID NO 21
<211> LENGTH: 32
<212> TYPE: DNA
<213> ORGANISM: Artificial Sequence
<220> FEATURE:
<223> OTHER INFORMATION: #33 tune box

<400> SEQUENCE: 21
gtatagttgc gtggatatgg cacgcaagtt tc                                32

<210> SEQ ID NO 22
<211> LENGTH: 32
<212> TYPE: DNA
<213> ORGANISM: Artificial Sequence
<220> FEATURE:
<223> OTHER INFORMATION: #36 tune box

<400> SEQUENCE: 22
gtatagcggc gtggatatgg cacgctggtt tc                                32

<210> SEQ ID NO 23
<211> LENGTH: 32
<212> TYPE: DNA
<213> ORGANISM: Artificial Sequence
<220> FEATURE:
<223> OTHER INFORMATION: #41 tune box

<400> SEQUENCE: 23
gtataatggc gtggatatgg cacgctagtt tc                                32

<210> SEQ ID NO 24

```
<211> LENGTH: 32
<212> TYPE: DNA
<213> ORGANISM: Artificial Sequence
<220> FEATURE:
<223> OTHER INFORMATION: #46 tune box

<400> SEQUENCE: 24
gtataattgc gtggatatgg cacgcaagtt tc                                    32

<210> SEQ ID NO 25
<211> LENGTH: 32
<212> TYPE: DNA
<213> ORGANISM: Artificial Sequence
<220> FEATURE:
<223> OTHER INFORMATION: #54 tune box

<400> SEQUENCE: 25
gtataattgc gtggatatgg cacgcgagtt tc                                    32

<210> SEQ ID NO 26
<211> LENGTH: 32
<212> TYPE: DNA
<213> ORGANISM: Artificial Sequence
<220> FEATURE:
<223> OTHER INFORMATION: #61 tune box

<400> SEQUENCE: 26
gtataatcgc gtggatatgg cacgcgagtt tc                                    32

<210> SEQ ID NO 27
<211> LENGTH: 32
<212> TYPE: DNA
<213> ORGANISM: Artificial Sequence
<220> FEATURE:
<223> OTHER INFORMATION: #69 tune box

<400> SEQUENCE: 27
gtataactgc gtggatatgg cacgcgggtt tc                                    32
```